US011066341B2

(12) United States Patent
Yoon et al.

(10) Patent No.: US 11,066,341 B2
(45) Date of Patent: Jul. 20, 2021

(54) MICROBIAL CONSORTIA

(71) Applicant: AMVAC Chemical Corporation, Newport Beach, CA (US)

(72) Inventors: Sung-Yong H. Yoon, Lake Oswego, OR (US); Kathleen Swords, Boise, ID (US); D. Ry Wagner, Pleasant Hill, OR (US); Xing Liang Liu, Davis, CA (US)

(73) Assignee: AMVAC Chemical Corporation, Newport Beach, CA (US)

( * ) Notice: Subject to any disclaimer, the term of this patent is extended or adjusted under 35 U.S.C. 154(b) by 102 days.

(21) Appl. No.: 16/072,026

(22) PCT Filed: Aug. 31, 2016

(86) PCT No.: PCT/US2016/049618
§ 371 (c)(1),
(2) Date: Jul. 23, 2018

(87) PCT Pub. No.: WO2017/131821
PCT Pub. Date: Aug. 3, 2017

(65) Prior Publication Data
US 2019/0029263 A1    Jan. 31, 2019

Related U.S. Application Data

(60) Provisional application No. 62/289,020, filed on Jan. 29, 2016.

(51) Int. Cl.
| | | |
|---|---|---|
| C12N 1/20 | (2006.01) | |
| C05F 11/08 | (2006.01) | |
| C12N 1/14 | (2006.01) | |
| A01N 63/32 | (2020.01) | |
| A01N 63/20 | (2020.01) | |
| A01N 63/22 | (2020.01) | |
| A01N 63/25 | (2020.01) | |
| A01N 63/28 | (2020.01) | |
| A01N 63/00 | (2020.01) | |

(52) U.S. Cl.
CPC .............. *C05F 11/08* (2013.01); *A01N 63/20* (2020.01); *A01N 63/22* (2020.01); *A01N 63/25* (2020.01); *A01N 63/28* (2020.01); *A01N 63/32* (2020.01); *C12N 1/14* (2013.01); *C12N 1/20* (2013.01)

(58) Field of Classification Search
CPC ......... A01N 63/00; A01N 25/12; C05F 11/08; C12N 1/14; C12N 1/20
USPC .......................................... 504/101; 424/400
See application file for complete search history.

(56) References Cited

U.S. PATENT DOCUMENTS

| | | | |
|---|---|---|---|
| 2012/0329650 A1 | 12/2012 | Lopez-Cervantes | |
| 2015/0282483 A1* | 10/2015 | Sawada | A01N 43/56 504/100 |
| 2016/0145564 A1* | 5/2016 | Miyamoto | C05F 11/08 435/252.5 |

FOREIGN PATENT DOCUMENTS

| | | | |
|---|---|---|---|
| CN | 102665436 | 9/2012 | |
| CN | 102946735 | 2/2013 | |
| CN | 104735983 | 6/2015 | |
| CN | 107532139 | 1/2018 | |
| CN | 107787360 | 3/2018 | |
| CN | 107849516 | 3/2018 | |
| WO | WO 2011/076759 A1 | 6/2011 | |
| WO | WO-2011076759 A1 * | 6/2011 | ............. C11B 1/025 |
| WO | WO 2011/157747 A1 | 12/2011 | |
| WO | WO 2013/148278 A1 | 10/2013 | |
| WO | WO 2014/207927 A1 | 12/2014 | |
| WO | WO 2016/135698 A1 | 9/2016 | |
| WO | WO 2016/135699 A1 | 9/2016 | |
| WO | WO 2016/135700 A1 | 9/2016 | |
| WO | WO 2018/045004 A1 | 3/2018 | |

OTHER PUBLICATIONS

Bueno-Solano et al., "Chemical and biological characteristics of protein hydrolysates from fermented shrimp by-products," *Food Chemistry* vol. 112, pp. 671-675, 2009.

Declaration of Dr. Jaime Lopez-Cervantes, executed on Oct. 18, 2011, submitted in International App. No. PCT/EP2010/070285 on Oct. 28, 2011 (2 pages).

Mensah, "HYT Biofertilizers and Biochar Effects on the Growth, Yield and Fruit Quality of Okra in the Forest Ecological Zone of Ghana," Thesis submitted to University of Ghana, Legon, Jun. 2013 (106 pages).

\* cited by examiner

*Primary Examiner* — Johann R Richter
*Assistant Examiner* — Courtney A Brown
(74) *Attorney, Agent, or Firm* — Klarquist Sparkman, LLP

(57) ABSTRACT

Disclosed herein are microbial consortia and compositions including microbes for example for use in agricultural or biodegradation applications. In some embodiments, soil, plants, and/or plant parts (such as seeds, seedlings, shoots, roots, leaves, fruit, stems, or branches) are contacted with a disclosed microbial consortia or composition including microbes. The microbial consortia or microbe-containing compositions may be applied to soil, plant, and/or plant parts alone or in combination with additional components (such as chitin, chitosan, glucosamine, amino acids, and/or liquid fertilizer). In additional embodiments, the disclosed microbial consortia or compositions including microbes are used in methods of degrading biological materials, such as chitin-containing biological materials.

20 Claims, 6 Drawing Sheets

Specification includes a Sequence Listing.

MICROBIAL CONSORTIA

CROSS REFERENCE TO RELATED APPLICATIONS

This filing is the § 371 U.S. National Stage of International Application No. PCT/US2016/049618, filed Aug. 31, 2016, which was published in English under PCT Article 21(2), which in turn claims the benefit of U.S. Provisional Application No. 62/289,020, filed Jan. 29, 2016, which is incorporated herein by reference in its entirety.

FIELD

This disclosure relates to microbial consortia and methods of use of the microbes included in the consortia, particularly for biodegradation and agricultural processes and uses.

BACKGROUND

World food demand continues to increase under pressure of increasing population growth. However, agricultural workers are faced with shrinking amounts of land available for agriculture, soil depletion, and changing environmental conditions, among other challenges. Thus, there is a need to develop compositions and techniques that can increase food production. There is also a need to do so while decreasing the use of potentially harmful herbicides, insecticides, and fungicides.

SUMMARY

Disclosed herein are microbial consortia and compositions including microbes, for use in agricultural or biodegradation applications. In some embodiments, a microbial composition of the present disclosure is the microbial consortium deposited with the American Type Culture Collection (ATCC, Manassas, Va.) on Dec. 23, 2015 and assigned deposit number PTA-122728 (referred to herein as A1007), or a composition including some or all of the microbes in A1007. In other embodiments, a composition of the present disclosure includes cells from five or more microbial species selected from *Bacillus* spp., *Lactobacillus* spp., *Clostridium* spp., *Virgibacillus* spp., *Brevibacillus* spp., *Paenibacillus* spp., *Oceanobacillus* spp., *Lysinibacillus* spp., *Acetobacter* spp., *Rummeliibacillus* spp., and *Candida* spp. In additional embodiments, a composition of the present disclosure includes cells from five or more microbial species selected from *Bacillus* spp., *Lactobacillus* spp., *Clostridium* spp., *Streptomyces* spp., *Virgibacillus* spp., *Brevibacillus* spp., *Paenibacillus* spp., *Oceanobacillus* spp., *Lysinibacillus* spp., *Acetobacter* spp., *Rummeliibacillus* spp., and *Candida* spp.

In some embodiments, the composition further includes cells from one or more of *Pseudomonas* spp., *Desulfococcus* spp., *Desulfotomaculum* spp., *Marinobacter* spp., *Nitrosopumilus* spp., *Deinococcus* spp., *Azospirillum* spp., *Leptolyngbya* spp., *Ruminococcus* spp., *Acidisoma* spp., *Leptospirillum* spp., *Rhodoferax* spp., *Pseudomonas* spp., *Halorhabdus* spp., *Microbacterium* spp., *Sporosarcina* spp., *Nesterenkonia* spp., *Agrococcus* spp., *Xenococcus* spp., *Cytophaga* spp., *Actinomyces* spp., *Devosia* spp., *Candidatus* spp., *Aquabacterim* spp., *Bradyrhizobium* spp., *Microcoleus* spp., *Acetobacter* spp., *Brevibacterium* spp., *Methanosaeta* spp., and *Acremonium* spp.

In additional embodiments, the composition includes cells from two or more (such as 5, 10, 15, 20, 25, or more) of the microorganisms listed in Table 1. The disclosed compositions may also include additional components, including but not limited to chitin, chitosan, glucosamine, amino acids, fertilizers, and/or binding agents.

Also disclosed are agricultural uses of the disclosed microbial consortia or compositions. In some embodiments, the methods (uses) include contacting soil, plants, and/or plant parts (such as seeds, seedlings, shoots, leaves, stems, or branches) with a disclosed microbial consortium (such as A1007), a composition including some or all of the microbes from A1007, or a composition including cells of two or more of the microbial species listed in Table 1. The microbial consortia or microbe-containing compositions may be applied to soil, plant, and/or plant parts alone or in combination with additional components (such as chitin, chitosan, glucosamine, amino acids, and/or fertilizer, such as liquid fertilizer).

In additional embodiments, the disclosed microbial consortia or compositions including microbes are used in methods of degrading biological materials, such as chitin-containing biological materials. In some examples, the chitin-containing materials are mixed with a microbial consortium (such as A1007), or a composition including five or more of the microbial species listed in Table 1, and fermented to produce a fermented mixture. The fermented mixture optionally may be separated into solid and liquid fractions. These fractions can subsequently be used in agricultural applications, for instance in combination with the disclosed microbial consortia or compositions, or can be used in further degradation processes, for example to produce increased levels of the degradation products in the solid and/or liquid fractions.

The foregoing and other features of the disclosure will become more apparent from the following detailed description, which proceeds with reference to the accompanying figures.

SEQUENCE LISTING

Figure 1:
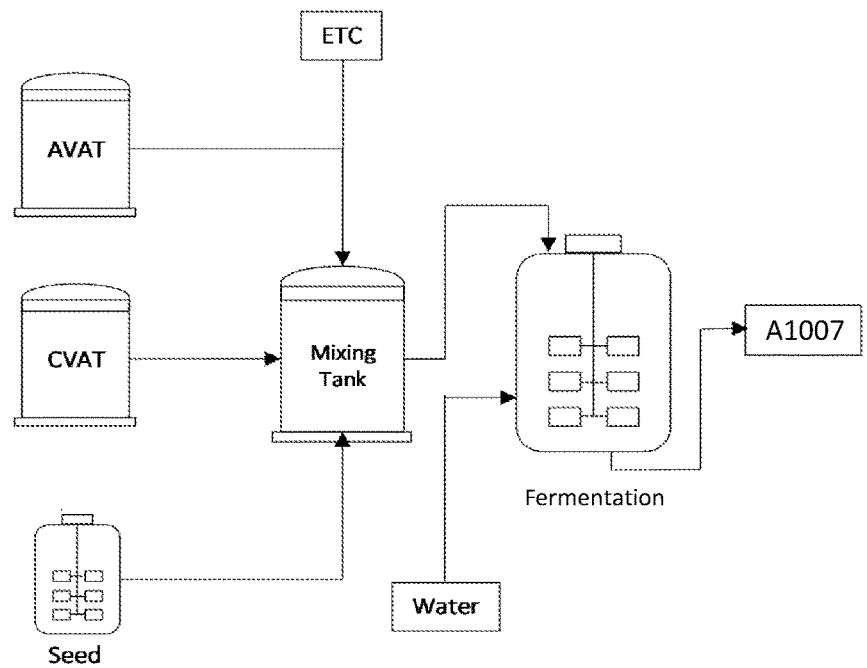
FIG. 1 is a schematic showing an exemplary fermentation process used to obtain the A1007 microbial consortium.

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Jul. 20, 2018, and is 35.4 kilobytes, which is incorporated by reference herein.

SEQ ID NO: 1 is a 16S rDNA nucleotide sequence from a microbe isolated from A1007 and identified as *Lactobacillus* sp. (*paracasei/casei*).

SEQ ID NO: 2 is a 16S rDNA nucleotide sequence from a microbe isolated from A1007 and identified as *Clostridium beijerinckii*.

SEQ ID NO: 3 is a 16S rDNA nucleotide sequence from a microbe isolated from A1007 and identified as *Acetobacter pasteurianum*.

SEQ ID NO: 4 is a 16S rDNA nucleotide sequence from a microbe isolated from A1007 and identified as *Lactobacillus buchneri*.

SEQ ID NO: 5 is a 16S rDNA nucleotide sequence from a microbe isolated from A1007 and identified as *Bacillus subtilis*.

SEQ ID NO: 6 is a 16S rDNA nucleotide sequence from a microbe isolated from A1007 and identified as *Paenibacillus cookii*.

SEQ ID NO: 7 is a 16S rDNA nucleotide sequence from a microbe isolated from A1007 and identified as *Lactobacillus vini*.

SEQ ID NO: 8 is a 16S rDNA nucleotide sequence from a microbe isolated from A1007 and identified as *Paenibacillus lautus*.

SEQ ID NO: 9 is a 16S rDNA nucleotide sequence from a microbe isolated from A1007 and identified as *Oceanobacillus oncorhynchi* subsp. *incaldanensis*.

SEQ ID NO: 10 is a 16S rDNA nucleotide sequence from a microbe isolated from A1007 and identified as *Bacillus amyloliquefaciens*.

SEQ ID NO: 11 is a 16S rDNA nucleotide sequence from a microbe isolated from A1007 and identified as highly similar to *Bacillus pocheonensis*.

SEQ ID NO: 12 is a 16S rDNA nucleotide sequence from a microbe isolated from A1007 and identified as *Paenibacillus chibensis*.

SEQ ID NO: 13 is a 16S rDNA nucleotide sequence from a microbe isolated from A1007 and identified as *Bacillus flexus*.

SEQ ID NO: 14 is a 16S rDNA nucleotide sequence from a microbe isolated from A1007 and identified as *Clostridium pasteurianum*.

SEQ ID NO: 15 is a 16S rDNA nucleotide sequence from a microbe isolated from A1007 and identified as *Virgibacillus halophilus*.

SEQ ID NO: 16 is a 16S rDNA nucleotide sequence from a microbe isolated from A1007 and identified as *Bacillus licheniformis*.

SEQ ID NO: 17 is a 16S rDNA nucleotide sequence from a microbe isolated from A1007 and identified as *Streptomyces griseus*.

DETAILED DESCRIPTION

In nature, the balance of microbial species in the soil is influenced by many factors, including soil type, soil fertility, moisture, competing microbes, and plants (Lakshmanan et al., *Plant Physiol.* 166:689-700, 2014). The interplay between microbial species and plants is further affected by agricultural practices, which can improve or degrade the soil microbiome (Adair et al., *Environ Microbiol Rep.* 5:404-413, 2013; Carbonetto et al., *PLoS One* 9:e99949, 2014; Ikeda et al., *Microbes Environ.* 29:50-59, 2014). Fertile or highly productive soils contain a different composition of native microbes than soil that is depleted of nutrients and linked to low crop productivity. Different microbial species are associated closely with plants, on the above-ground plant surfaces in the phyllosphere, at the root surface in the soil rhizosphere, or intimately as endophytes. Large-scale DNA analysis of these microbe associations has revealed unexpected phylogenetic complexity (Rincon-Florez et al., *Diversity* 5:581-612, 2013; Lakshmanan et al., *Plant Physiol.* 166:689-700, 2014). Studies have determined complex microbiomes can be correlated to plant productivity, crop yield, stress tolerance, secondary metabolite accumulation, and disease tolerance (Bhardwaj et al., *Microbial Cell Factories* 13:66-75, 2014; Vacheron et al., *Frontiers Plant Science* 4:1-19, 2014). Furthermore, plants can specifically select the microbial mixtures from the local environment and potentially fine-tune the microbiome at the level of crop variety (Hartmann et al., *Plant Soil* 321:235-257, 2009; Doornbos et al., *Agron. Sustain. Dev.* 32:227-243, 2012; Marasco et al., *PLoS One* 7:e48479, 2012; Peiffer et al., *Proc. Natl. Acad. Sci. USA* 110:6548-6553, 2013; Bulgarelli et al., *Ann. Rev. Plant Biol.* 64:807-838, 2014).

Root-associated microbes can promote plant and root growth by promoting nutrient cycling and acquisition, by direct phytostimulation, by mediating biofertilization, or by offering growth advantage through biocontrol of pathogens. Agriculturally useful populations include plant growth promoting rhizobacteria (PGPR), pathogen-suppressive bacteria, mycorrhizae, nitrogen-fixing cyanobacteria, stress tolerance endophytes, plus microbes with a range of biodegradative capabilities. Microbes involved in nitrogen cycling include the nitrogen-fixing *Azotobacter* and *Bradyrhizobium* genera, nitrogen-fixing cyanobacteria, ammonia-oxidizing bacteria (e.g., the genera *Nitrosomonas* and *Nitrospira*), nitrite-oxidizing genera such as *Nitrospira* and *Nitrobacter*, and heterotrophic-denitrifying bacteria (e.g., *Pseudomonas* and *Azospirillum* genera; Isobe and Ohte, *Microbes Environ.* 29:4-16, 2014). Bacteria reported to be active in solubilization and increasing plant access to phosphorus include the *Pseudomonas, Bacillus, Micrococcus*, and *Flavobacterium*, plus a number of fungal genera (Pindi et al., *J. Biofertil. Biopest.* 3:4, 2012), while *Bacillus* and *Clostridium* species help solubilize and mobilize potassium (Mohammadi et al., *J. Agric. Biol. Sci.* 7:307-316, 2012). Phytostimulation of plant growth and relief of biotic and abiotic stresses is delivered by numerous bacterial and fungal associations, directly through the production of stimulatory secondary metabolites or indirectly by triggering low-level plant defense responses (Gaiero et al., *Amer. J. Bot.* 100:1738-1750, 2013; Bhardwaj et al., *Microbial Cell Factories* 13:66-76, 2014).

In addition to activity in the environment, microbes can also deliver unique biodegradative properties in vitro, under conditions of directed fermentation. Use of specific microbial mixtures to degrade chitin and total protein can yield new bioactive molecules such as free L-amino acids, L-peptides, chitin, and chitosan known to enhance growth or boost stress tolerance via activation of plant innate immunity (Hill et al., *PLoS One* 6:e19220, 2011; Tanaka et al., *Plant Signal Behav.* E22598-147, 2013). Specific microbial communities can serve multiple tasks, by delivering unique fermentation breakdown products, which are themselves biologically beneficial to crops, plus the resultant microbial consortium, which can be delivered as an agricultural product to enhance crop productivity.

As described herein, consortia of aerobic and/or anaerobic microbes derived from fertile soil and marine sources have been successfully co-fermented and stabilized, offering direct growth and yield benefits to crops. Enzymatic activity of these microbial mixtures has further yielded fermentation products with chitin, glucosamine, protein, and/or amino acids. In some embodiments, direct delivery of microbial consortia and/or compositions can allow early root colonization and promote rhizosphere or endophytic associations. In some embodiments, benefits of delivery of microbial consortia to plants include one or more of increased root growth, increase root hair production, increased root surface area, stronger plants able to withstand transplantation shock, faster stand establishment, resistance to abiotic stress, and higher plant productivity and yield. Complex microbial mixes can span across plant species and genotypes, interacting with microbial soil communities to offer benefits to a wide range of crops growing under different agricultural conditions.

I. Terms

Unless otherwise noted, technical terms are used according to conventional usage. Definitions of common terms in molecular biology may be found in Krebs et al., *Lewin's Genes XI*, published by Jones and Bartlett Learning, 2012 (ISBN 1449659853); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 2011 (ISBN 8126531789); and George P. Rédei, *Encyclopedic Dictionary of Genetics, Genomics, and Proteomics*, 2nd Edition, 2003 (ISBN: 0-471-26821-6).

The following explanations of terms and methods are provided to better describe the present disclosure and to guide those of ordinary skill in the art to practice the present disclosure. The singular forms "a," "an," and "the" refer to one or more than one, unless the context clearly dictates otherwise. For example, the term "comprising a cell" includes single or plural cells and is considered equivalent to the phrase "comprising at least one cell." As used herein, "comprises" means "includes." Thus, "comprising A or B," means "including A, B, or A and B," without excluding additional elements. All publications, patent applications, patents, and other references mentioned herein are incorporated by reference in their entirety for all purposes. In case of conflict, the present specification, including explanations of terms, will control.

Although methods and materials similar or equivalent to those described herein can be used to practice or test the disclosed technology, suitable methods and materials are described below. The materials, methods, and examples are illustrative only and not intended to be limiting.

To facilitate review of the various embodiments of this disclosure, the following explanations of specific terms are provided:

Aquatic Animal: An animal that lives in salt or fresh water. In particular embodiments disclosed herein, an aquatic animal includes aquatic arthropods, such as shrimp, krill, copepods, barnacles, crab, lobsters, and crayfish. In other embodiments, an aquatic animal includes fish. An aquatic animal by-product includes any part of an aquatic animal, particularly parts resulting from commercial processing of an aquatic animal. Thus, in some examples, aquatic animal by-products include one or more of shrimp cephalothorax or exoskeleton, crab or lobster exoskeleton, or fish skin or scales.

Contacting: Placement in direct physical association, including both in solid and liquid form. For example, contacting can occur with one or more microbes (such as the microbes in a microbial consortium) and a biological sample in solution. Contacting can also occur with one or more microbes (such as the microbes in a microbial consortium) and soil, plants, and/or plant parts (such as foliage, stem, seedling, roots, and/or seeds).

Culturing: Intentional growth of one or more organisms or cells in the presence of assimilable sources of carbon, nitrogen and mineral salts. In an example, such growth can take place in a solid or semi-solid nutritive medium, or in a liquid medium in which the nutrients are dissolved or suspended. In a further example, the culturing may take place on a surface or by submerged culture. The nutritive medium can be composed of complex nutrients or can be chemically defined.

Fermenting: A process that results in the breakdown of complex organic compounds into simpler compounds, for example by microbial cells (such as bacteria and/or fungi). The fermentation process may occur under aerobic conditions, anaerobic conditions, or both (for example, in a large volume where some portions are aerobic and other portions are anaerobic). In some non-limiting embodiments, fermenting includes the enzymatic and/or non-enzymatic breakdown of compounds present in aquatic animals or aquatic animal by-products, such as chitin.

Liquid fertilizer: An aqueous solution or suspension containing soluble nitrogen. In some examples, the soluble nitrogen in a liquid fertilizer includes an organic source of nitrogen such as urea, or urea derived from anhydrous ammonia (such as a solution of urea and ammonium nitrate (UAN)). Aqua ammonia (20-32% anhydrous ammonia) can also be used. In other examples, the soluble nitrogen in a liquid fertilizer includes nitrogen-containing inorganic salts such as ammonium hydroxide, ammonium nitrate, ammonium sulfate, ammonium pyrophosphate, ammonium thiosulfate or combinations of two or more thereof. In some embodiments the liquid fertilizer includes a non-naturally occurring nitrogen source (such as ammonium pyrophosphate or ammonium thiosulfate) and/or other non-naturally occurring components.

Common liquid non-natural fertilizer blends are specified by their content of nitrogen-phosphate-potassium (N—P—K percentages) and include addition of other components, such as sulfur or zinc. Examples of human-made blends include 10-34-0, 10-30-0 with 2% sulfur and 0.25% zinc (chelated), 11-37-0, 12-30-0 with 3% sulfur, 2-4-12, 2-6-12, 4-10-10, 3-18-6, 7-22-5, 8-25-3, 15-15-3, 17-17-0 with 2% sulfur, 18-18-0, 18-18-0 with 2% sulfur, 28-0-0 UAN, 9-27-0 with 2% sulfur and potassium thio-sulfate.

Microbe: A microorganism, including but not limited to bacteria, archaebacteria, fungi, and algae (such as microalgae). In some examples, microbes are single-cellular organisms (for example, bacteria, cyanobacteria, some fungi, or some algae). In other examples, the term microbes includes multi-cellular organisms, such as certain fungi or algae (for example, multicellular filamentous fungi or multicellular algae).

Microbial composition: A composition (which can be solid, liquid, or at least partially both) that includes at least one microbe (or a population of at least one microbe). In some examples, a microbial composition is one or more microbes (or one or more populations of microbes) in a liquid medium (such as a storage, culture, or fermentation medium), for example, as a suspension in the liquid medium. In other examples, a microbial composition is one or more microbes (or one or more populations of microbes) on the surface of or embedded in a solid or gelatinous medium (including but not limited to a culture plate), or a slurry or paste.

Microbial consortium: A mixture, association, or assemblage of two or more microbial species, which in some instances are in physical contact with one another. The microbes in a consortium may affect one another by direct physical contact or through biochemical interactions, or both. For example, microbes in a consortium may exchange nutrients, metabolites, or gases with one another. Thus, in some examples, at least some of the microbes in a consortium may be metabolically interdependent. Such interdependent interactions may change in character and extent through time and with changing culture conditions.

II. Microbial Consortia and Compositions

Disclosed herein are several microbial consortia. An exemplary microbial consortium of the present disclosure was deposited with the American Type Culture Collection (ATCC, Manassas, Va.) on Dec. 23, 2015 and assigned deposit number PTA-122728, referred to herein as A1007. The A1007 consortium includes at least *Bacillus* spp., *Lactobacillus* spp., *Clostridium* spp., *Streptomyces* spp., *Virgibacillus* spp., *Brevibacillus* spp., *Paenibacillus* spp., *Oceanobacillus* spp., *Lysinibacillus* spp., *Acetobacter* spp., *Rummeliibacillus* spp., and *Candida* spp. Also disclosed herein are consortia or microbial compositions including two or more (such as 2 or more, 5 or more, 10 or more, 20 or more, or 50 or more) or all of the microbes in A1007. In some embodiments, a microbial composition disclosed herein is a defined composition, for example a composition including specified microbial species and optionally, additional non-microbial components (including but not limited to, salts, trace elements, chitin, chitosan, glucosamine, and/or amino acids). In some examples, the microbial consortia or compositions include aerobic and anaerobic microbes.

As discussed below, identity of at least some microbes present in A1007 were determined using colony purification and DNA sequence analysis (e.g., 16S rDNA sequencing, Example 4) and/or microarray analysis (Example 14). Additional techniques for identifying microbes present in a microbial mixture or consortium are known to one of ordinary skill in the art, including 1) nucleic acid-based methods which are based on the analysis and differentiation of microbial DNA (such as DNA microarray analysis of nucleic acids, metagenomics, or in situ hybridization coupled with fluorescent-activated cell sorting (FACS)); 2) biochemical methods which rely on separation and identification of a range biomolecules including fatty acid methyl esters analysis (FAME), Matrix-assisted laser desorption ionization-time of flight (MALDI-TOF) mass spectrometry analysis, or cellular mycolic acid analysis by High Performance Liquid Chromatography (MYCO-LCS) analysis; and 3) microbiological methods which rely on traditional tools (such as selective growth and microscopic examination) to provide more general characteristics of the community as a whole, and/or narrow down and identify only a small subset of the members of that community.

In some examples, microbes in a mixture or consortium are separated (for example using physical size and/or cell sorting techniques) followed by deep DNA or full genome sequencing of the resulting microbes (or subgroups or subpopulations of microbes). Use of a different microarray or use of other identification techniques may identify presence of different microbes (more, fewer, or different microbial taxa or species) due to differences in sensitivity and specificity of the analysis technique chosen. In addition, various techniques (including microarray analysis or PCR DNA analysis) may not detect particular microbes (even if they are present in a sample), for example if probes and/or primers capable of detecting particular microbes are not included in the analysis. In addition, one of ordinary skill in the art will recognize that microbial classification and naming may change over time and result in reclassification and/or renaming of microbes.

In some embodiments, a composition of the present disclosure includes cells from five or more microbial species selected from *Bacillus* spp., *Lactobacillus* spp., *Clostridium* spp., *Virgibacillus* spp., *Brevibacillus* spp., *Paenibacillus* spp., *Oceanobacillus* spp., *Lysinibacillus* spp., *Acetobacter* spp., *Rummeliibacillus* spp., and *Candida* spp. In some examples, the composition includes cells selected from 5 or more, 6 or more, 7 or more, 8 or more, 9 or more, 10 or more, or all of *Bacillus* spp., *Lactobacillus* spp., *Clostridium* spp., *Virgibacillus* spp., *Brevibacillus* spp., *Paenibacillus* spp., *Oceanobacillus* spp., *Lysinibacillus* spp., *Acetobacter* spp., *Rummeliibacillus* spp., and *Candida* spp. In additional embodiments, a composition of the present disclosure includes cells from five or more microbial species selected from *Bacillus* spp., *Lactobacillus* spp., *Clostridium* spp., *Streptomyces* spp., *Virgibacillus* spp., *Brevibacillus* spp., *Paenibacillus* spp., *Oceanobacillus* spp., *Lysinibacillus* spp., *Acetobacter* spp., *Rummeliibacillus* spp., and *Candida* spp. In some examples, the composition includes cells selected from 5 or more, 6 or more, 7 or more, 8 or more, 9 or more, 10 or more, 11 or more, or all of *Bacillus* spp., *Lactobacillus* spp., *Clostridium* spp., *Streptomyces* spp., *Virgibacillus* spp., *Brevibacillus* spp., *Paenibacillus* spp., *Oceanobacillus* spp., *Lysinibacillus* spp., *Acetobacter* spp., *Rummeliibacillus* spp., and *Candida* spp.

In other embodiments the disclosed microbial consortia or compositions include, consist essentially of, or consist of two or more (such as 5 or more, 6 or more, 7 or more, 8 or more, 9 or more, 10 or more, 11 or more, 12 or more, 13 or more, 14 or more, 15 or more, 20 or more, or all) of the microbes listed in Table 1. In further embodiments, the disclosed microbial consortia or compositions include, consist essentially of, or consist of two or more (such as 5 or more, 10 or more, 15 or more, or all) of the microbes having 16S rDNA sequence with at least 95% identity (such as at least 96%, 97%, 98%, 99%, or more) with SEQ ID NOs: 1-17.

TABLE 1

Microbes

| Microbe | Exemplary species |
|---|---|
| *Acetobacter* spp. | *Acetobacter pasteurianum* |
| *Bacillus* spp. | *Bacillus amyloliquefaciens, Bacillus pocheonensis, Bacillus clausii, Bacillus subtilis, Bacillus circulans, Bacillus licheniformis, Bacillus pumilus, Bacillus flexus, Bacillus subterraneus, Bacillus oceanisediminis, Bacillus firmus* |
| *Brevibacillus* spp. | *Brevibacillus brevis* |
| *Candida* spp. | *Candida ethanolica* |
| *Clostridium* spp. | *Clostridium nitrophenolicum, Clostridium pasteurianum, Clostridium beijerinckii, Clostridium sphenoides, C. tyrobutyricum* |
| *Lactobacillus* spp. | *Lactobacillus casei, Lactobacillus vini, Lactobacillus buchneri, Lactobacillus casei* |
| *Lysinibacillus* spp. | *Lysinibacillus xylanilyticus, Lysinibacillus fusiformis* |
| *Oceanobacillus* spp. | *Oceanobacillus oncorhynchi* subsp. *incaldanensis* |
| *Paenibacillus* spp. | *Paenibacillus chibensis, Paenibacillus lautus, Paenibacillus validus, Paenibacillus cookii, Paenibacillus anaericanus, Paenibacillus agaridevorans, Paenibacillus timonensis, Paenibacillus cineris, Paenibacillus rhizoospherae, Paenibacillus brevis, Paenibacillus favisporus* |
| *Rummeliibacillus* spp. | *Rummeliibacillus pycnus, Rummeliibacillus stabekisii* |
| *Streptomyces* spp. | *Streptomyces griseus* |
| *Virgibacillus* spp. | *Virgibacillus halophilus* |

In some embodiments, the microbial composition includes an increased amount of particular microbes compared to A1007. For example, culture of A1007 with liquid fertilizer (for example, as described in Example 5) leads to an increase in the amount of one or more of *Bacillus* spp. (e.g., one or more of *Bacillus circulans, Bacillus pocheonensis, Bacillus flexus, Bacillus subterraneus, Bacillus firmus*, or *Bacillus oceanisediminis*), *Brevibacillus* spp. (e.g. *Brevibacillus brevis*), *Lysinibacillus* spp. (e.g., *Lysinibacillus fusiformis*), *Paenibacillus* spp. (e.g. *Paenibacillus validus, Paenibacillus anaericanus, Paenibacillus agaridevorans, Paenibacillus cineris, Paenibacillus rhizoospherae, Paenibacillus favisporus*, or *Paenibacillus timonensis*), *Clostridium* spp. (e.g. *Clostridium nitrophenolicum, Clostridium tyrobutyricum*, or *Clostridium sphenoides*), *Oceanobacillus* spp. (e.g. *Oceanobacillus oncorhynchi* subsp. *incaldanensis*), *Rummeliibacillus* spp. (e.g. *Rummeliibacillus stabekisii*), and/or *Virgibacillus* spp. (e.g. *Virgibacillus halophilus*) in the microbial composition.

In some examples, the microbial composition includes at least about 10% more of one or more of *Bacillus* spp. (e.g., one or more of *Bacillus circulans, Bacillus pocheonensis, Bacillus flexus, Bacillus subterraneus, Bacillus firmus*, or *Bacillus oceanisediminis*), *Brevibacillus* spp. (e.g. *Brevibacillus brevis*), *Lysinibacillus* spp. (e.g., *Lysinibacillus fusiformis*), *Paenibacillus* spp. (e.g. *Paenibacillus validus, Paenibacillus anaericanus, Paenibacillus agaridevorans, Paenibacillus cineris, Paenibacillus rhizoospherae, Paenibacillus favisporus*, or *Paenibacillus timonensis*), *Clostridium* spp. (e.g. *Clostridium nitrophenolicum, Clostridium tyrobutyricum*, or *Clostridium sphenoides*), *Oceanobacillus* spp. (e.g. *Oceanobacillus oncorhynchi* subsp. *incaldanensis*), *Rummeliibacillus* spp. (e.g. *Rummeliibacillus stabekisii*), and/or *Virgibacillus* spp. (e.g. *Virgibacillus halophilus*) compared to A1007.

The consortia or compositions can optionally include cells from one or more additional microbial species, beyond those listed in Table 1. In some embodiments the additional microbes include *Azotobacter* spp. (e.g., *Azotobacter vinelandii* and/or *Azotobacter chroococcum*) or *Rhizobium* spp. (e.g., *Rhizobium japonicus* and/or *Rhizobium leguminosarum*). Additional microbes include, but are not limited to one or more of *Desulfococcus* spp., *Desulfotomaculum* spp., *Marinobacter* spp. (e.g., *Marinobacter bryozoorum*), *Nitrosopumilus* spp., *Ruminococcus* spp. (e.g., *Ruminococcus flavefaciens*), *Pseudomonas* spp. (e.g., *Pseudomonas fluorescens* or *Pseudomonas putida*), *Deinococcus* spp., *Azospirillum* spp., *Aquabacterium* spp., *Clostridium* spp. (e.g., *Clostridium butyricum*), *Cytophaga* spp., *Microbacterium* spp. (e.g., *Microbacterium testaceum*), *Lysinibacillus* (e.g., *Lysinibacillus sphaericus*), *Sporosarcina* spp., *Nesterenkonia* spp., *Agrococcus* spp. (e.g., *Agrococcus terreus*), *Acremonium* spp. (e.g., *Acremonium bacillisporum*), *Bacillus* sp. (e.g., *Bacillus megaterium, Bacillus thuringiensis, Bacillus licheniformis, Bacillus subtilis, Bacillus cereus*), *Lactobacillus* spp. (e.g., *Lactobacillus acidophilus*), *Acetobacter* spp. (e.g., *Acetobacter aceti*), *Acidisoma* spp., *Azotobacter* spp. (e.g., *Azotobacter vinelandii* or *Azotobacter chroococcum*), *Treponema* spp. (e.g., *Treponema primitia*), *Bradyrhizobium* spp. (e.g., *Bradyrhizobium elkanii*), *Lactococcus* spp., *Leptolyngbya* spp., *Leptospirillum* spp. (e.g. *Leptospirillum ferrodiazotrophum*), *Halorhabdus* spp., *Xenococcus* spp., *Paenibacillus* spp. (e.g., *Paenibacillus amyloticus*), *Pediococcus* (e.g., *Pediococcus pentosceus*), *Proteus* spp. (e.g., *Proteus vulgaris*), *Rhizobium* (e.g., *Rhizobium japonicus* or *Rhizobium leguminosarum*), *Rhodoferax* spp., *Streptomyces* spp. (e.g., *Streptomyces griseus*), *Streptococcus* spp., *Trichoderma* spp. (e.g., *Trichoderma harzianum*), *Microcoleus* spp., *Micrococcus* spp. (e.g., *Micrococcus luteus*), *Nitrobacter* spp., *Nitrosomonas* spp., *Nitrospira* spp., *Actinomyces* spp., *Devosia* spp., *Brevibacterium* spp., *Methanosaeta* spp., *Saccharomyces* spp. (e.g., *Saccharomyces cerevisiae*), *Penicillium* spp. (e.g., *Penicillium roqueforti*), *Monascus* (e.g., *Monascus ruber*), *Aspergillus* spp. (e.g., *Aspergillus oryzae*), *Arthrospira* spp. (e.g., *Arthrospira platensis*), and *Ascophyllum* spp. (e.g., *Ascophyllum nodosum*). Suitable additional microbes can be identified by one of skill in the art, for example, based on characteristics desired to be included in the consortia or compositions.

The disclosed compositions may include one or more further components in addition to the microbes, including by not limited to salts, metal ions, and/or buffers (for example, one or more of $KH_2PO_4$, $K_2HPO_4$, $CaCl_2$, $MgSO_4$, $FeCl_3$, NaMoO$_4$, and/or Na$_2$MoO$_4$), trace elements (such as sulfur, sulfite, sulfate, copper, or selenium), micronutrients (such as boron (B), zinc (Zn), manganese (Mn), iron (Fe), copper (Cu), molybdenum (Mo), chlorine (Cl)), vitamins (such as B vitamins or vitamin K), sugars (such as sucrose, glucose, or fructose), chitin, chitosan, glucosamine, protein, and/or amino acids. Additional components that may also be included in the compositions include HYT B, HYT C, and/or HYT D, one or more fertilizers (e.g., liquid fertilizer), one or more pesticides, one or more fungicides, one or more herbicides, one or more insecticides, one or more plant hormones, one or more plant elicitors, or combinations of two or more of these components.

In some embodiments, the disclosed microbial consortia or compositions (such as those including five or more microbial species in the microbial consortia described herein) are in a liquid medium (such as a culture or fermentation medium) or inoculum. In other embodiments, the microbial consortia or compositions (for example, compositions including five or more microbial species listed in Table 1) are present on a solid or gelatinous medium (such as a culture plate) containing or supporting the microbes.

In yet other embodiments, the microbial consortia or compositions (such as a composition including five or more microbial species listed in Table 1) are present in a dry formulations, such as a dry powder, pellet, or granule. Dry formulations can be prepared by adding an osmoprotectant (such as a sugar, for example, trehalose and/or maltodextrin) to a microbial composition in solution at a desired ratio. This solution is combined with dry carrier or absorptive agent, such as wood flour or clay, at the desired concentration of microbial composition (such as 2-30%, for example, 2.5-10%, 5-15%, 7.5-20%, or 15-30%). Granules can be created by incorporating clay or polymer binders that serve to hold the granules together or offer specific physical or degradation properties. Granules can be formed using rotary granulation, mixer granulation, or extrusion, as a few possible methods. In other examples, dry formulations can be prepared by spraying or soaking the liquid microbial composition on/in a solid carrier such as bentonite or coating the liquid microbial composition directly on a fertilizer granule. Additional methods for preparing dry formulations including one or more microbial species are known to one of ordinary skill in the art, for example as described in *Formulation of Microbial Biopesticides: Beneficial Microorganisms, Nematodes and Seed Treatments*, Burges, ed., Springer Science, 1998; Bashan, *Biotechnol. Adv.* 16:729-770, 1998; Ratul et al., *Int. Res. J. Pharm.* 4:90-95, 2013.

In some examples, microbial consortia or compositions including microbes may be maintained at a temperature supporting growth of the microbe(s), for example at about 25-45° C. (such as about 30-35° C., about 30-40° C., or about 35-40° C.). In other examples, the compositions are stored at temperatures at which the microbe(s) are not growing or are inactive, such as less than 25° C. (for example, 4° C., −20° C., −40° C., −70° C., or below). One of skill in the art can formulate the compositions for cold storage, for example by including stabilizers (such as glycerol). In still further examples, the compositions are stored at ambient temperatures, such as about 0-35° C. (for examples, about 10-30° C. or about 15-25° C.).

III. Biodegradation Processes

Figure 2:
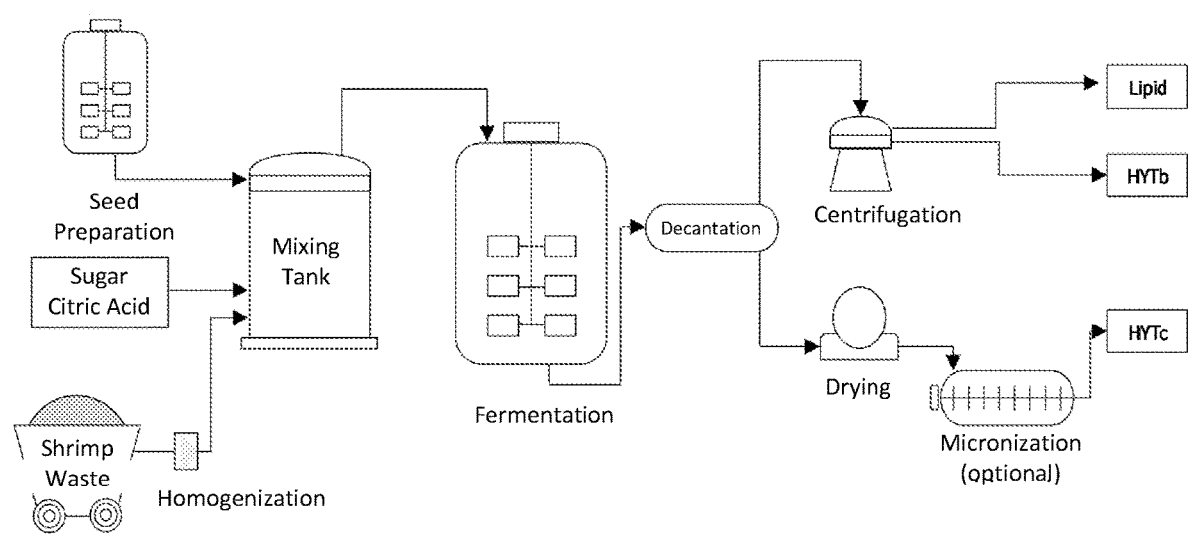
FIG. 2 is a schematic showing an exemplary process for biodegradation of a chitin-containing biological material (exemplified as shrimp waste) with a disclosed microbial consortium or microbial composition.
Figure 3:
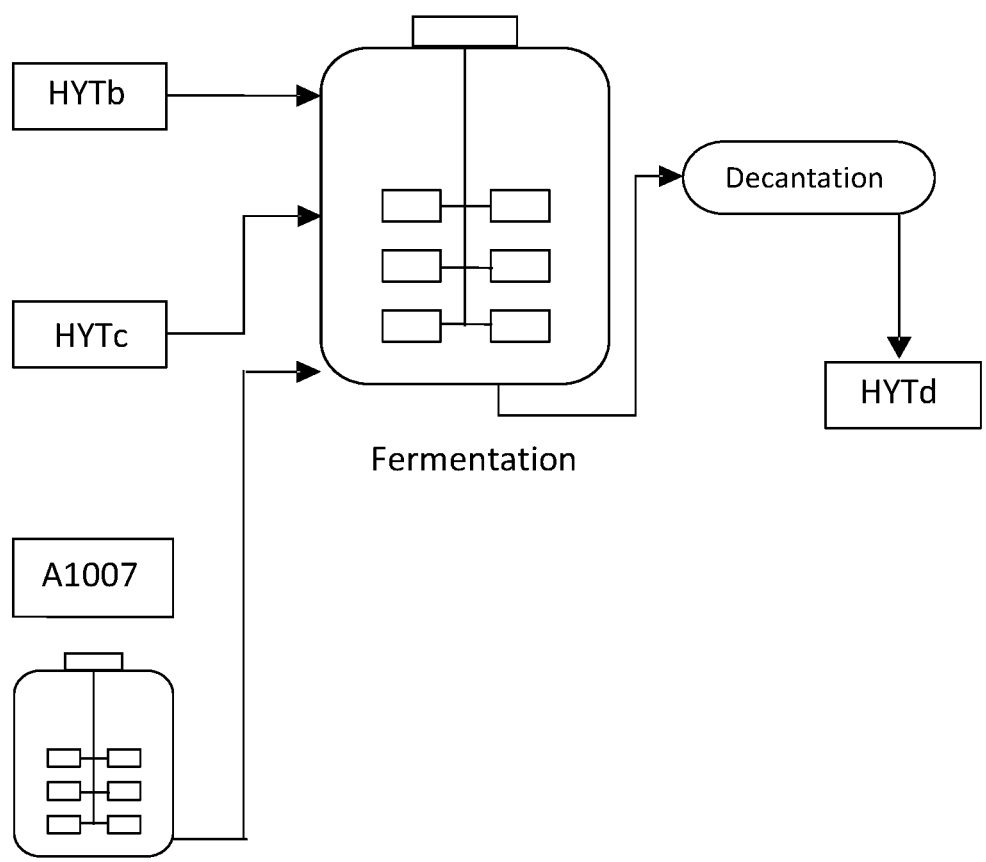
FIG. 3 is a schematic showing an exemplary process for biodegradation of chitin with a disclosed microbial consortium (such as A1007) or microbial composition.

The disclosed microbial consortia and compositions can be used to degrade biological materials, such as chitin-rich materials, for example, aquatic animals or aquatic animal by-products, insects, or fungi. Thus, disclosed herein are methods including mixing one or more of the disclosed microbial consortia or compositions with a chitin-containing biological material to form a mixture, and fermenting the mixture. In some embodiments, the methods also include separating the mixture into solid, aqueous, and optionally, lipid fractions (FIG. 2) after fermentation.

In some embodiments, a biodegradation process disclosed herein includes mixing a microbial consortium (such as A1007, a composition including some or all of the microbes in A1007, or a composition including five or more of the microbial species in Table 1) with one or more chitin-containing biological materials. Chitin-containing biological materials include, but are not limited to, aquatic animals or aquatic animal by-products, insects, or fungi. In some examples, the chitin-containing biological material is an aquatic animal, such as an aquatic arthropod (for example, a member of Class Malacostraca). Aquatic arthropods for use in the disclosed methods include shrimp, crab, lobster, crayfish, or krill; mixtures of two or more are contemplated. In some examples, the entire aquatic animal (such as an aquatic arthropod) or aquatic animal by-products are used in the biodegradation methods disclosed herein. Aquatic animal by-products include any part of an aquatic animal, such as any part produced by processing of the aquatic animal. In some examples, an aquatic animal by-product is all or a portion of an aquatic animal exoskeleton, such as shrimp, crab, crayfish, or lobster shell. In other examples, an aquatic animal by-product is a part of an aquatic animal, for example, shrimp cephalothoraxes.

In other examples, the chitin-containing biological material includes fungi, such as fungi from Phylum Zygomycota, Basidiomycota, Ascomycota, or Deuteromycota. Particular exemplary fungi include *Aspergillus* spp., *Penicillium* spp., *Trichoderma* spp., *Saccharomyces* spp., and *Schizosaccharomyces* spp. Thus, baker, brewer, and distiller waste streams can provide sources for chitin-containing biological material. In still further examples, the chitin-containing biological material includes insects that contain chitin in their exoskeletons, such as grasshoppers, crickets, beetles, and other insects. Byproducts of the processing of such insects are also contemplated to be sources of chitin.

The chitin-containing biological material is mixed with a composition including the microbes described in Section II above (such as the microbial consortium A1007 or other consortium or composition described in Section II) to form a substantially homogeneous mixture. In some examples, the chitin-containing biological material is ground, crushed, minced, milled, or otherwise dispersed prior to mixing with the microbes or microbial consortia described herein. In particular examples, the mixture contains about 10-50% (such as about 10-20%, about 20-30%, about 30-40%, about 25-40%, for example about 25%, about 30%, about 35%, about 40%, about 45%, or about 50%) chitin-containing material (such as shrimp heads and/or shells) (w/v) in inoculum containing about 0.1-5% (such as about 0.1-1%, about 0.5-2%, about 1-2%, about 2-3%, about 0.1%, about 0.2%, about 0.3%, about 0.5%, about 0.8%, about 1%, about 1.25%, about 1.5%, about 1.75%, about 2%, about 2.5%, about 3%, about 4%, or about 5%) microbes (v/v).

In some examples, the inoculum, chitin-containing biological material, and a sugar (or other carbon source) are mixed together, for example by stirring or agitation. In other examples, one or more of the microbes in the microbial composition or consortium is optionally activated prior to mixing with the chitin-containing biological material and fermentation. Activation is not required for the methods disclosed herein. Adjustments to the time and/or temperature of the fermentation can be made by one of skill in the art, depending on whether the microbes are activated prior to fermentation. Activation of the microbial composition can be by incubating an inoculum of the microbes with a carbon source (such as a sugar, for example, glucose, sucrose, fructose, or other sugar) at a temperature and for a sufficient period of time for the microbes to grow. In some examples, an inoculum of the microbes (such as a microbial consortium or composition described herein) has a concentration of about 0.05-5% v/v (for example, about 0.5-5%, about 0.5-2%, about 1-2%, or about 2-3%) in a liquid medium. The inoculum is diluted in a solution containing about 0.1-1% sugar (for example, about 0.1-0.5%, about 0.1-0.3%, about 0.2-0.6%, or about 0.5-1%, such as about 0.1%, about 0.2%, about 0.3%, about 0.4%, about 0.5%, about 0.6%, about 0.7%, about 0.8%, about 0.9%, or about 1%) and incubated at ambient temperatures, for example about 20-40° C. (such as about 20° C., about 25° C., about 30° C., about 35° C., or about 40° C.) for about 1-5 days (such as about 24 hours, about 48 hours, about 72 hours, about 96 hours, or about 120 hours). In other examples, activation of the microbial composition can be activated by incubating an inoculum of the microbes at a temperature and for a sufficient period of time for the microbes to grow, for example, incubation at about 20-40° C. (such as about 25-35° C.) for 12 hours to 5 days (such as 1-4 days or 2-3 days). In some non-limiting examples, the microbes are considered to be activated when the culture reaches an optical density of >0.005 at 600 nm.

After mixing of the chitin-containing biological material and the microbes or microbial consortium (which are optionally activated), the mixture is fermented. In some examples, the pH of the mixture is measured prior to fermentation. The pH is adjusted to a selected range (e.g., pH about 3 to about 4 or about 3.5 to 4), if necessary, prior to fermentation. The mixture is incubated at a temperature of about 20-40° C. (for example, about 30°-36° C., such as about 30° C., about 31° C., about 32° C., about 33° C., about 34° C., about 35° C., about 36° C., about 37° C., about 38° C., about 39° C., or about 40° C.) for about 1-30 days (such as about 3-28 days, about 7-21 days, about 3, 5, 7, 10, 14, 16, 20, 24, 28, or 30 days). The mixture is agitated periodically (for example, non-continuous agitation). In some examples, the mixture is agitated for a period of time every 1-7 days, for example every 1, 2, 3, 4, 5, 6, or 7 days. In some non-limiting examples, the fermentation proceeds until the titratable acidity (TTA) is about 3-5% and the pH is about 4-5.

Following the fermentation, the resulting fermented mixture is separated into at least solid and liquid fractions. In some examples, the fermentation is passed from the tank to settling equipment. The liquid is subsequently decanted and centrifuged. In one non-limiting example, the fermented mixture is centrifuged at 1250 rpm (930×g) for 15 minutes at about 5° C. to obtain liquid and lipid (e.g., pigment) fractions. The liquid (or aqueous) fraction obtained from the biodegradation process can be stored at ambient temperature. In some non-limiting examples, a sugar is added to the liquid fraction, for example at 1-10% v/v.

The liquid fraction may include components such as protein, amino acids, glucosamine, trace elements (such as calcium, magnesium, zinc, copper, iron, and/or manganese), and/or enzymes (such as lactic enzymes, proteases, lipases, and/or chitinases). In some non-limiting examples, the liquid fraction contains (w/v) about 1-5% total amino acids, about 3-7% protein, about 0.1-2% nitrogen, less than about 0.2% phosphorus, about 0.5-1% potassium, about 4-8% carbon, about 0.2-1% calcium, less than about 0.2% magnesium, less than about 0.2% sodium, and/or about 0.1-0.4% sulfur. In additional non-limiting examples, the liquid fraction includes about 0.01-0.2% glucosamine (for example, about 0.1% or less). The liquid fraction also may contain one or more microbes (e.g., from the inoculum used to start the fermentation process) and/or trace amounts of chitosan or chitin. The liquid fraction is in some examples referred to herein as "HYT B."

The solid fraction obtained from the biodegradation process contains chitin (for example, about 50-70% or about 50-60% chitin). The solid fraction may also contain one or more of trace elements (such as calcium, magnesium, zinc, copper, iron, and/or manganese), protein or amino acids, and/or one or more microbes from the inoculum used to start the fermentation process. The solid fraction is in some examples referred to herein as "HYT C." HYT C is optionally micronized to form micronized chitin and residual chitin. In some non-limiting examples, the solid fraction contains (w/v) about 9-35% total amino acids, about 30-50% crude protein, about 5-10% nitrogen, about 0.3-1% phosphorus, less than about 0.3% potassium, about 35-55% carbon, about 0.5-2% calcium, less than about 0.1% magnesium, about 0.1-0.4% sodium, and/or about 0.2-0.5% sulfur.

In some examples, a lipid fraction is also separated from the solid and liquid fractions. The lipid fraction is the upper phase of the liquid fraction. The lipid fraction contains compounds such as sterols, vitamin A and/or vitamin E, fatty acids (such as DHA and/or EHA), and in some examples, carotenoid pigments (for example, astaxanthin). The lipid fraction may be used for a variety of purposes, including but not limited to production of cosmetics or nutritional products.

In additional embodiments, chitin is fermented with a microbial consortium (such as A1007 or some or all of the microbes in A1007) or a composition containing five or more of the microbial species in Table 1. In some examples chitin (such as HYT C, or micronized and/or residual chitin produced as described above) is mixed with a microbial consortium or composition containing microbes described herein and protein hydrolyzate (e.g., HYT B), and fermented to form a fermented mixture. At least a portion of the chitin in the starting mixture is digested as a result of the fermentation. In some examples, the mixture is incubated at a temperature of about 20-40° C. (for example, about 30°-35° C., such as about 30° C., about 31° C., about 32° C., about 33° C., about 34° C., about 35° C., about 36° C., about 37° C., about 38° C., about 39° C., or about 40° C.) for about 1 day to 30 days (such as about 2-28 days, about 4-24 days, about 16-30 days, about 10-20 days, or about 12-24 days). In some examples, the mixture is agitated periodically (for example, non-continuous agitation). In other examples, the mixture is continuously agitated. In one non-limiting example, the mixture is agitated for about 1-12 hours daily (such as about 2-8 hours or about 4-10 hours). The pH of the fermentation mixture may be monitored periodically. In some examples, the pH is optionally maintained at about 4-5. In some examples, the fermentation proceeds until Total Titratable Acidity (TTA) is at least about 1-10% (such as about 2-8%, about 4-8%, or about 5-10%).

Following the fermentation, the resulting fermented mixture is separated into at least solid and liquid fractions, for example by decanting, filtration, and/or centrifugation. The liquid fraction resulting from fermentation of HYT B and chitin with the microbial composition is in some examples referred to herein as "HYT D." In some non-limiting examples, the liquid fraction contains (w/v) about 0.5-2% total amino acids, about 3-7% protein, about 0.5-1% nitrogen, less than about 0.1% phosphorus, about 0.4-1% potassium, about 3-7% carbon, less than about 0.5% calcium, less than about 0.1% magnesium, less than about 0.3% sodium, and/or about less than about 0.3% sulfur. In addition, HYT D contains less than about 50% chitin (such as less than about 45%, less than about 40%, less than about 35%, or less than about 30% chitin) and less than 2% glucosamine (such as less than about 1.5% or less than about 1% glucosamine). In other examples, HYT D contains about 25-50% chitin and about 0.5-2% glucosamine.

IV. Processes for Treating Soil, Plants, and/or Seeds

The disclosed microbial consortia, compositions containing microbes, and/or products disclosed herein (such as HYT B, HYT C, and/or HYT D) can be used to treat soil, plants, or plant parts (such as roots, stems, foliage, seeds, or seedlings). In some examples, treatment with the microbial consortia, compositions containing microbes, and/or products improves plant growth, improves stress tolerance and/or increases crop yield. Methods of producing HYT B, HYT C, and HYT D are described above and also in U.S. Pat. No. 8,748,124 and International Pat. App. Publ. No. WO 2012/175738, both of which are incorporated herein by reference in their entirety.

In some embodiments the methods include contacting soil, plants (such as plant foliage, stems, roots, seedlings, or other plant parts), or seeds with a consortium (such as A1007) or a composition including the microbes present in one or more of the disclosed microbial consortia or compositions. The methods may also include growing the treated plants, plant parts, or seeds and/or cultivating plants, plant parts or seeds in the treated soil.

The microbes are optionally activated before application. In some examples, activation of the microbes is as described in Section III, above. In other examples, the microbes are activated by mixing 100 parts water and 1 part microbial consortium or composition and incubating at about 15-40° C. (such as about 20-40° C., about 15-30° C., or about 25-35° C.) for about 12 hours-14 days (such as about 1-14 days, 3-10 days, 3-5 days, or 5-7 days). The activation mixture optionally can also include 1 part HYT B, if the microbial consortium or composition is to be applied in combination with HYT B.

In other embodiments, the methods include contacting soil, plants (or plant parts), or seeds with a product of the disclosed microbial consortia or compositions, such as HYT B, HYT C, HYT D, or combinations thereof. In still further embodiments, the methods include contacting soil, plants, or seeds with a disclosed microbial consortium or composition including the disclosed microbes and one or more of HYT B, HYT C, and HYT D (such as one, two, or all of HYT B, HYT C, and HYT D). HYT B, HYT C, and/or HYT D may be separately applied to the soil, plants (or plant parts), and/or seeds, for example sequentially, simultaneously, or substantially simultaneously with the disclosed microbial consortia or compositions containing microbes.

In some examples, the methods further include contacting the soil, plants (or plant part), or seeds with one or more additional components including but not limited to chitin, chitosan, glucosamine, protein, amino acids, liquid fertilizer, one or more pesticides, one or more fungicides, one or more herbicides, one or more insecticides, one or more plant hormones, one or more plant elicitors, or combinations of two or more thereof. The additional components may be included in the composition including the microbes or in the microbial consortia disclosed herein, or may be separately applied to the soil, plants (or plant parts), and/or seeds, for example sequentially, simultaneously, or substantially simultaneously with the disclosed consortia or compositions containing microbes.

In particular embodiments, a microbial consortium or composition is combined with a liquid fertilizer (for example a solution or suspension containing soluble nitrogen). In some examples, the liquid fertilizer includes an organic source of nitrogen such as urea, or a nitrogen-containing inorganic salt such as ammonium hydroxide, ammonium nitrate, ammonium sulfate, ammonium pyrophosphate, ammonium thiosulfate or combinations thereof. Aqua ammonia (20-24.6% anhydrous ammonia) can also be used as the soluble nitrogen. In some examples, the microbial consortium or composition is combined with the liquid fertilizer (for example, mixed with the liquid fertilizer) immediately before use or a short time before use (such as within 10 minutes to 24 hours before use, for example, about 30 minutes, 1 hour, 2 hours, 3 hours, 4 hours, 6 hours, 8 hours, 12 hours, 16 hours, 18 hours, or 24 hours before use). In other examples, the microbial consortium or composition is combined with the liquid fertilizer (for example mixed with the liquid fertilizer) at least 24 hours before use (such as 24 hours to 6 months, for example, at least 36 hours, at least 48 hours, at least 72 hours, at least 96 hours, at least one week, at least two weeks, at least four weeks, at least eight weeks, or at least 12 weeks before use).

In some examples, the amount of the composition(s) to be applied (for example, per acre or hectare) is calculated and the composition is diluted in water (or in some examples, liquid fertilizer) to an amount sufficient to spray or irrigate the area to be treated (if the composition is a liquid, such as microbial consortia or compositions, HYT B, or HYT D). In other examples, the composition can be mixed with diluted herbicides, insecticides, pesticides, or plant growth regulating chemicals. If the composition to be applied is a solid (such as a dry formulation of microbes, HYT C, chitin, glucosamine, chitosan, or amino acids), the solid can be applied directly to the soil, plants, or plant parts or can be suspended or dissolved in water (or other liquid) prior to use. In some examples, HYT C is dried and micronized prior to use.

The disclosed microbial compositions (alone or in combination with other components disclosed herein, such as HYT B, HYT C, and/or HYT D) can be delivered in a variety of ways at different developmental stages of the plant, depending on the cropping situation and agricultural practices. In some examples, a disclosed microbial composition and HYT B are mixed and diluted with liquid fertilizer and applied at the time of seed planting at a rate of 0.5 to 1 to 2 liters each per acre, or alternatively are applied individually. In other examples, a disclosed microbial composition and HYT B are mixed and diluted and applied at seed planting, and also applied to the soil near the roots at multiple times during the plant growth, at a rate of 0.5 to 1 to 2 liters each per acre, or alternatively are applied individually. In still further examples, a disclosed microbial composition and HYT B are diluted and delivered together through drip irrigation at low concentration as seedlings or transplants are being established, delivered in flood irrigation, or dispensed as a diluted mixture with nutrients in overhead or drip irrigation in greenhouses to seedlings or established plants, or alternatively are applied individually. In additional examples, a disclosed microbial composition is added to other soil treatments in the field, such as addition to insecticide treatments, to enable ease-of-use. In other examples, such as greenhouses, a disclosed microbial composition and HYT B are used individually or together, combined with liquid fertilizer (such as fish fertilizer) and other nutrients and injected into overhead water spray irrigation systems or drip irrigation lines over the course of the plant's growth. In one greenhouse example, a disclosed microbial composition and HYT B are used together, for example, diluted and applied during overhead irrigation or fertigation at a rate of 0.25 to 1 liter at seedling germination, followed by 0.25 to 1 liter mid-growth cycle with fertigation, and final 0.25 to 1 liter fertigation 5-10 days end of growth cycle.

In some embodiments, a disclosed microbial composition or consortium (such as A1007) and HYT B are applied together or individually (for example sequentially) to promote yield, vigor, typeness, quality, root development, or stress tolerance in crops. In one specific example where the crop is corn, 1 to 2 L/acre microbial composition is added in-furrow with liquid fertilizer at seed planting, or applied as a side dress during fertilization after V3 stage, followed by 0.5 to 2 L/acre of HYT B as a foliar spray after V5 stage, added and diluted with herbicides, foliar pesticides, micronutrients, or fertilizers.

In another specific example where the crop is potato, 1 to 3 L/acre of microbial composition is diluted and used either alone or with 1 to 3 L/acre of HYT B at tuber planting; this can be followed by subsequent soil applications of the microbial composition and HYT B before tuberization, either alone (e.g., sequentially) or together. After plant emergence, potato foliar applications of HYT B at 1 to 2 L/acre can be applied, either diluted alone or mixed with herbicide, foliar pesticide, micronutrient, and/or fertilizer treatments, and applied during the growing season one time, two times, three times, four times, or more.

In yet another specific example where the crop is cotton, 1 to 2 L/acre of microbial composition is applied in-furrow at planting, as a side dress, or 2×2 (2 inches to side and 2 inches below seed), with or without fertilizer. At first white cotton bloom, foliar treatments of 0.5 to 2 L/acre HYT B can be applied, diluted alone or combined with other nutrient, herbicide, or pesticidal treatments.

In another particular example where the crop is wheat, the microbial composition (1 to 2 L/acre) is applied after winter dormancy (S4 stage) and HYT B applied foliarly (0.5 to 2 L/acre; S4 to S10 stage).

In an example where the crop is sugarcane, one application method uses a disclosed microbial composition and HYT B at 2 to 4 L/acre each, applied to the soil during cane planting or as a side dress, with foliar HYT B applied at 1 to 2 L/acre, mixing with water or fertilizers or micronutrients.

HYT B can be used alone as a foliar treatment in all crops to improve traits such as plant stress tolerance, vegetative vigor, harvest quality and yield. In an example where the crop is corn, HYT B can be applied at ½ to 1 L/acre, one or multiple times, mixing with water or pesticides or herbicides. In another example, HYT B can be used to treat wheat as a foliar spray, mixed with water or pesticides or herbicides, at a rate of ½ to 1 L/acre, applying one or multiple times.

In all crops, HYT C may be added to the soil at a rate of about 0.5-2 kg/acre (such as about 0.5 kg/acre, about 1 kg/acre, about 1.5 kg/acre, or about 2 kg/acre) at the time of crop establishment or planting. In other examples, HYT C is added to a drip irrigation solution of a disclosed microbial composition and HYT B or is added to fertilization applications containing a disclosed microbial composition and HYT B in greenhouses, such as the examples above.

In additional embodiments, HYT D (alone or in combination with the microbes or other components disclosed herein) is used at about 1-20 L/hectare (such as about 1-15 L/hectare, about 3-10 L/hectare, or about 3-5 L/hectare). In other examples, HYT D (alone or in combination with the microbes or other components disclosed herein) is used as a seed treatment to enhance crop yield and performance (for example, about 1-10 L/kg seed, such as about 1-3 L/kg, about 3-5 L/kg, or about 5-10 L/kg). Alternatively, HYT D can be used in the soil (alone or in combination with the microbes or other components disclosed herein) at about 1-3 L/hectare to increase plant growth, for example to help plants remain productive under conditions of stress.

In some examples, treatment of soil, seeds, plants, or plant parts with a composition comprising the microbes in a disclosed microbial consortium increases plant growth (such as overall plant size, amount of foliage, root number, root diameter, root length, production of tillers, fruit production, pollen production, or seed production) by at least about 5% (for example, at least about 10%, at least about 30%, at least about 50%, at least about 75%, at least about 100%, at least about 2-fold, at least about 3-fold, at least about 5-fold, at least about 10-fold, or more). In other examples, the disclosed methods result in increased crop production of about 10-75% (such as about 20-60% or about 30-50%) compared to untreated crops. Other measures of crop performance include quality of fruit, yield, starch or solids content, sugar content or brix, shelf-life of fruit or harvestable product, production of marketable yield or target size, quality of fruit or product, grass tillering and resistance to foot traffic in turf, pollination and fruit set, bloom, flower number, flower lifespan, bloom quality, rooting and root mass, crop resistance to lodging, abiotic stress tolerance to heat, drought, cold and recovery after stress, adaptability to poor soils, level of photosynthesis and greening, and plant health. To determine efficacy of products, controls include the same agronomic practices without addition of microbes, performed in parallel.

The disclosed methods and compositions can be used in connection with any crop (for example, for direct crop treatment or for soil treatment prior to or after planting). Exemplary crops include, but are not limited to alfalfa, almond, banana, barley, broccoli, canola, carrots, citrus and orchard tree crops, corn, cotton, cucumber, flowers and ornamentals, garlic, grapes, hops, horticultural plants, leek, melon, oil palm, onion, peanuts and legumes, pineapple, poplar, pine and wood-bearing trees, potato, raspberry, rice, sesame, sorghum, soybean, squash, strawberry, sugarcane, sunflower, tomato, turf and forage grasses, watermelon, wheat, and eucalyptus.

The following examples are provided to illustrate certain particular features and/or embodiments. These examples should not be construed to limit the disclosure to the particular features or embodiments described.

Example 1

Microbial Consortium A1007

This example describes production of microbial consortium A1007.

A1007 was produced from a seed batch of microbes that originally were derived from fertile soils and additional microbes (such as *Bacillus* spp.) (see, e.g., U.S. Pat. No. 8,748,124, incorporated herein by reference). The "seed" culture was mixed with a suspension containing 5.5% w/w whey protein and 1.2% w/w yogurt in water ("C vat") and a suspension containing 0.1% w/w spirulina and 0.1% w/w kelp extract in water ("A vat"). The A vat and C vat suspensions were each individually prepared 3 days before mixing with the seed culture and incubated at ambient temperature. The seed culture, C vat, and A vat were mixed at a proportion of about 81:9:9. After mixing, a suspension of additional components containing about 70% v/v molasses, 0.5% v/v HYT B, 0.003% w/v Arabic gum, and 0.02% w/v brewer's yeast (S. cerevisiae) were mixed with the mixture of the seed culture, C vat, and A vat, and additional water at a ratio of about 16:34:50. The mixture was fermented for about 7 days at ambient temperature (about 19-35° C.). After 7 days, the tanks were aerated for 30 minutes every other day. Additional water was added (about 10% more v/v) and fermentation was continued under the same conditions for about 10 more days. Additional water was added (about 4% more v/v) and fermentation was continued for about 7 more days, at which time samples were collected for analysis and deposit with the ATCC. The resulting consortium (referred to as A1007) was subsequently stored in totes at ambient temperature. A schematic diagram showing an exemplary method for production of A1007 is shown in FIG. 1.

Example 2

Analysis of Microbial Count in A1007 by Plating

This example describes analysis of the viable microbial load present in A1007 by spread-plating under aerobic and anaerobic conditions.

Samples (1 L to 5 L) were collected from a well-mixed tote of A1007 using a sanitized handheld siphon drum pump. Analysis of the microbial count was conducted using a spread-plating methodology to determine the colony forming units (CFU) in the sample(s). All samples were stored at room temperature in light and air tight containers. After vigorous mixing of the sample to ensure the contents were evenly dispersed 1 mL was retained. From this aliquot, 0.1 mL was aseptically collected and mixed with 9.9 mL of sterile water in a culture tube ($10^{-2}$ dilution). The tube was then vortexed (e.g., 60 seconds at 2000 rpm) and 10 fold serial dilutions prepared in water (up to the $1:10^9$ dilution). One hundred microliters of each dilution was subsequently spread on semi-solid media in 100 mm Petri plates using a sterile L-shaped spreader. Plates containing Standard Method Agar (SMA; BD #247940), Nutrient Agar (NA; BD #213000) or other selected growth medium (Table 2) were used. The inoculated plates were then incubated in temperature controlled chambers at 22° C. to 35° C. For evaluation of anaerobic microbe counts, plates were first placed in anaerobic boxes (e.g. BD GasPak™ EZ Container Systems, BD Diagnostics) before incubation at the desired temperature(s). In some instances, the aliquot to be tested was first incubated in sterile peptone water for a period of up to 3 days at temperatures up to 35° C. prior to performing serial dilutions and plating as described above.

TABLE 2

Semi-solid media used to isolate microbes from A1007

| Genus | Semi-solid Medium* |
|---|---|
| Bacillus spp. | NA, YPD, SMA, AMA, AMAG |
| Lactobacillus spp. | YPD, MRS, NA, SMA |
| Virgibacillus spp. | YPD |
| Brevibacillus spp. | RMA |
| Paenibacillus spp. | AMA, NA, RMA, MRS |
| Clostridium spp. | SMA, RCM |
| Oceanobacillus spp. | RMA |
| Lysinibacillus spp. | NA, MRS, YPD |
| Acetobacter spp. | YPD, PA |
| Rummeliibacillus spp. | NA |
| Candida spp. | YPD |

*NA: nutrient agar (BD #213000); SMA: standard method agar (BD #247940); YPD: yeast peptone dextrose (BD#242720); AMA: azotobacter medium agar (HIMEDIA #M372); AMAG: azotobacter medium agar supplement with 10 g/L glucose (HIMEDIA #M371); RCM: reinforce clostridium medium (BD #218081); RMA: rhizobium medium agar (HIMEDIA #M408); PA: Pikovskaya's medium (HIMEDIA #M520); MRS: Lactobacilli MRS (BD# 288210).

Post-incubation, all colonies on selected plates were counted using a colony counter such as Quebec® Dark-Field Colony Counter (Reichert) and CFU)/mL were calculated. For peptone-treated A1007, plating showed $8.73 \times 10^9$ CFU/mL under aerobic conditions and $1.4 \times 10^9$ CFU/mL under anaerobic conditions. For A1007 which was not incubated with peptone, plating showed $3.28 \times 10^5$ CFU/mL under aerobic conditions and $3.55 \times 10^5$ CFU/mL under anaerobic conditions.

Example 3

Analysis of Microbes in A1007 by Colony Purification

This example describes colony purification and analysis of a subset of the microbes present in A1007.

After vigorous mixing of the A1007 sample to ensure the contents were evenly dispersed, a 1 mL aliquot was obtained. From this aliquot, 0.1 mL was directly plated on semi-solid media using the spread-plating method described above. Media of various compositions were selected for both selective and non-selective growth conditions. Table 2 summarizes media used for isolation of microorganisms from A1007. Plates were incubated either aerobically or anaerobically as described in Example 2 at temperatures varying from 22° C. to 35° C.

Selection of microbial strains for further investigation was based on classical macroscopic and microscopic characteristics of the colonies growing on semi-solid media (Bergey's Manual of Systematics of Archaea and Bacteria; Editor(s): William B. Whitman, 2012). Criteria such as colony color, density or morphology were used. In addition, cell morphology and differential staining such as Gram staining were used to study individual cells derived from colonies using a bright field digital microscope.

Example 4

Analysis of Microbes in A1007 by Sequencing

This example describes analysis of microbes in A1007 by sequencing 16S rDNA.

Genomic DNA was extracted from isolated colonies obtained as described in Example 3. 16S rDNA was amplified by PCR and sequenced, for example using MICROSEQ ID microbial identification system (Applied Biosystems/Life Technologies, Grand Island, N.Y.). Sequencing data was analyzed, for example using SHERLOCK DNA software (MIDI Labs, Newark, Del.). Sequences were compared against public databases to identify the microbes. 16S rDNA sequences obtained are provided herein as SEQ ID NOs: 1-17.

Example 5

Growth of Microbes in Nitrogen Fertilizer

This example describes selecting subpopulations of the microbial consortium using different growth conditions, such as exposure to liquid fertilizer. This example also demonstrates the tolerance of the microbes to high concentrations of nitrogen fertilizers and the utility of combining the microbe consortium with fertilizers used in agriculture.

A1007 was combined with liquid urea-ammonia-nitrogen fertilizer (UAN 32) fertilizer in a ratio of 80:1 (fertilizer: microbes) in 50 mL culture tubes maintained at room temperature and in the dark. Small aliquots (0.1 mL) were collected up to 3 weeks from the start of the incubation and processed for colony isolation using the spread-plating/ serial dilution method described in Example 3. Plating and isolation of colonies was performed as described above using both selective and non-selective media. Microbial colonies were selected based on colony morphology, color, size, and growth conditions, including Gram staining. Cleanly separated colonies were sent to MIDI Labs Inc. (Newark, Del.) for sequencing of the 16S variable region ribosomal DNA for species identification (as described in Example 4).

Purified isolates were identified and are listed in Table 3, which indicates the recovery of these strains under either non-UAN or UAN growth conditions. A species level match was assigned if the % GD (generic difference) between the unknown and the closest match was less than the approximate average % GD between species within that particular genetic family, which is usually 1%. A genus level match was assigned when the sequence did not meet the requirements for a species level match, but still clustered within the branching of a well-defined genus (1%<% GD<3%).

TABLE 3

Microbes identified by sequencing of colonies from
A1007 cultured in the presence or absence of UAN.

| Microbe | Without UAN | Plus UAN |
|---|---|---|
| *Bacillus circulans* | X | X |
| *Bacillus pocheonensis* | X | X |
| *Bacillus flexus* | X | X |
| *Bacillus subterraneus* |  | X |
| *Bacillus oceanisediminis* |  | X |
| *Bacillus firmus* |  | X |
| *Brevibacillus brevis* | X | X |
| *Clostridium nitrophenolicum* | X | X |
| *Clostridium tyrobutyricum* |  | X |
| *Clostridium sphenoides* |  | X |
| *Lysinibacillus fusiformis* |  | X |
| *Oceanobacillus oncorhynchi* subsp. *incaldanensis* | X | X |
| *Paenibacillus validus* | X | X |
| *Paenibacillus anaericanus* | X | X |
| *Paenibacillus agaridevorans* |  | X |
| *Paenibacillus timonensis* |  | X |
| *Paenibacillus cineris* |  | X |
| *Paenibacillus rhizoospherae* |  | X |
| *Paenibacillus favisporus* |  | X |
| *Rummeliibacillus stabekisii* |  | X |
| *Virgibacillus halophilus* |  | X |

Example 6

Biodegradation of Chitin-Containing Materials

This example describes exemplary methods for biodegradation of chitin-containing biological materials using the microbial consortium A1007. However, one skilled in the art will appreciate that methods that deviate from these specific methods can also be used for successful biodegradation of chitin-containing biological materials.

Shrimp by-products are obtained from shrimp processing plants and transported in closed, chilled containers. After inspection of the raw material quality, the shrimp by-products are processed to reduce particle size to about 3-5 mm. Pre-activated (e.g., with sugar (about 2.5 g/L) A1007 microbial cultures (about 0.2-100 mL/L) and sucrose (about 5 g/L) are mixed with the homogenized shrimp by-product (about 50 g/L) and agitated until the mixture is homogeneous. With continuous agitation, the temperature is maintained at ambient temperature (about 19-35° C.) and the pH is adjusted to 3.5-4.0 with citric acid. The mixed ingredients are transferred into a sanitized fermentation tank (25,000 L) and fermented at 30-36° C. for 120 hrs. Agitation is applied for 30 minutes at least two times a day. During the fermentation process, the pH is monitored, and the total titratable acidity (TTA, %) is determined by titration with 0.1 N NaOH. The fermentation is stopped when the TTA is about 3.5% and/or the pH is about 4-5.

The fermented cultures are fed to a continuous decanter. The separated solid layer from the decanting step is subject to centrifugation to remove the lipid layer. The purified liquid (HYT B) is mixed with sugar (such as molasses, 10% v/v), then stored in holding tanks or dispensed to totes. The solid materials from the decanting step are dried with superheated air at 120° C. until their moisture content is below 8%, then ground to 200 mesh. The dried product (HYT C) is packaged in bags or sacks.

Example 7

Biodegradation of Chitin

This example describes exemplary methods for biodegradation of chitin using the microbial consortium A1007. However, one skilled in the art will appreciate that methods that deviate from these specific methods can also be used for successful biodegradation of chitin.

A1007 microbial culture is pre-activated with sugar (about 2.5 g/L) in a 10,000 L tank for three days. The activated inoculum is mixed with protein hydrolysate such as HYT B (about 500 mL/L) and chitin (HYT C e.g., produced as described in Example 6). The mixture is gently mixed for 1 hour to achieve complete homogenization. The mixture is fermented for 20 days at ambient temperature (e.g., about 19-35° C.) with agitation for about 8 hours daily and pH monitoring (pH 4.0-5.0). Samples may be collected periodically, for instance every two days, for quantification of glucosamine and optionally chitosan. After fermentation is complete, the mixture is filtered through a filter that retains particles of 300 mesh, primarily the remaining chitin. The filtrate is retained and bottled after product characterization.

Example 8

Treatment of Field Corn with Microbial Compositions

This example describes a representative method for obtaining increased corn crop yield, using a microbial consortium. One skilled in the art will appreciate that methods that deviate from these specific methods can also be used for increasing crop yield.

Treatment of field corn with a microbial composition similar to A1007, or with HYT B, showed a strong increase in final harvestable yield. All agronomic practices of fertilization, cultivation, weed control, and pest control, were identical and side-by-side for the microbial composition- or HYT B-treated plots (Test) and control (Check) plots.

Figure 4A:
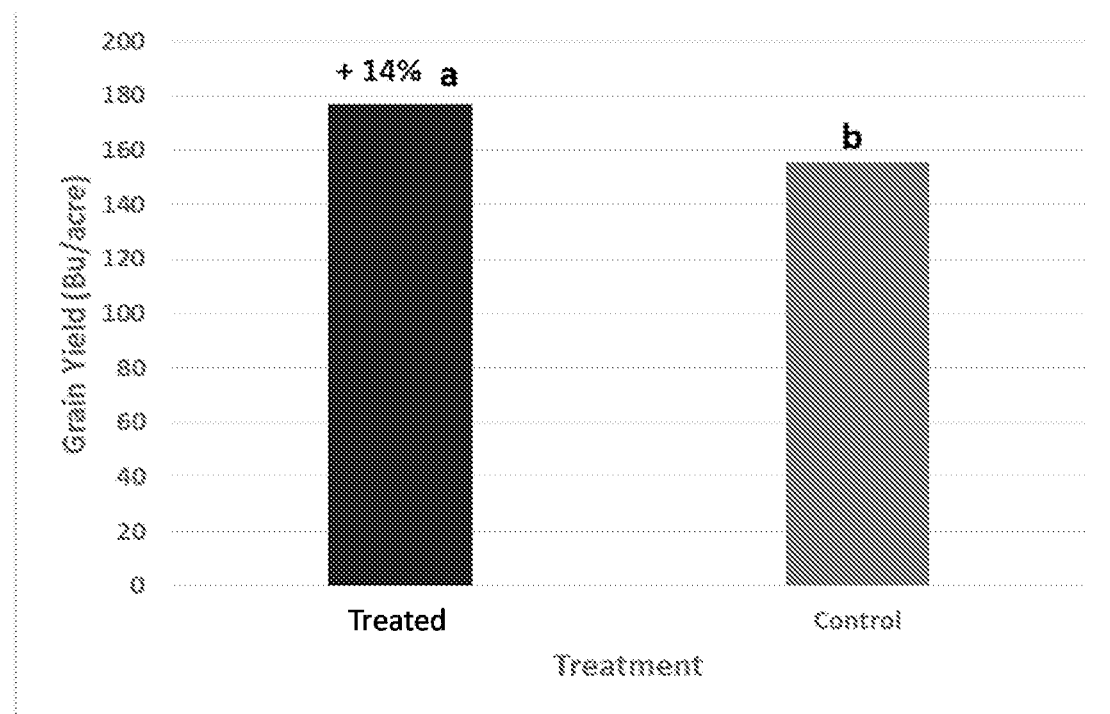
FIGS. 4A-4C are graphs showing effect on grain yield (bushels per acre) of treatment of corn with a microbial composition (FIG. 4A), HYT B (FIG. 4B), or a microbial composition under water stress conditions (FIG. 4C).

Trial A demonstrated that, when evaluated in a replicated plot design trial, a single soil inoculation of corn with the microbial composition at 1 L/acre in furrow at V6 stage, delivered with 28% nitrogen fertilizer via drip irrigation, provided a 14% increase yield over the untreated control across five replicated plots (FIG. 4A).

Figure 4B:
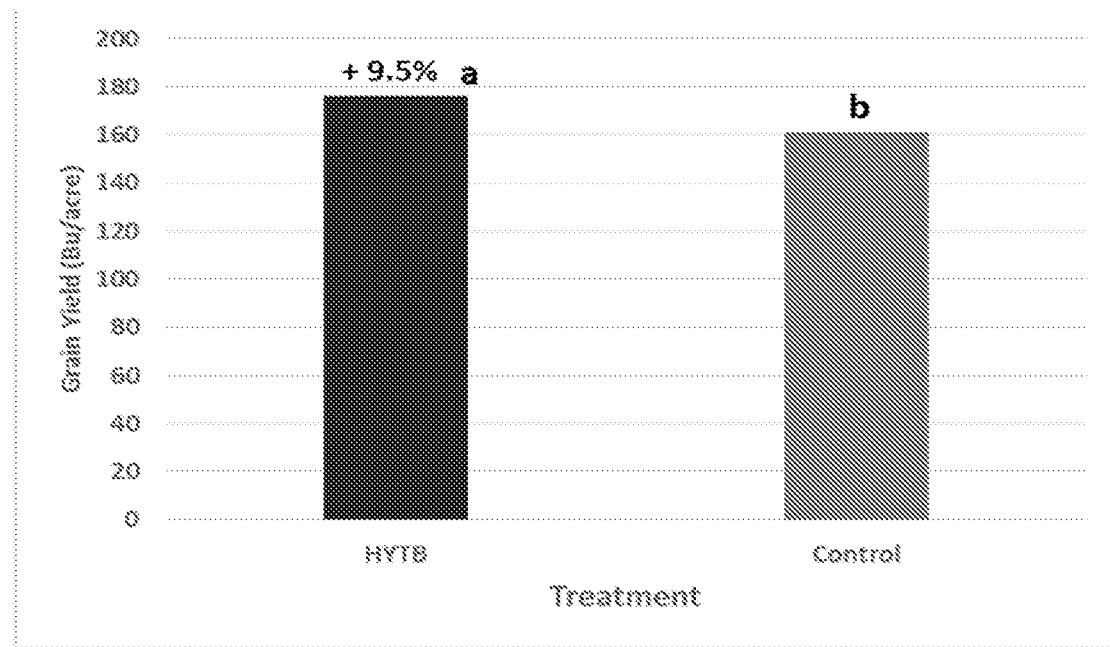

Trial B showed that HYT B, when used alone as a foliar treatment in corn, also provided a 9.5% yield increase when compared to the untreated control when tested in a randomized, replicated plot design trial. HYT B was foliar sprayed over two applications of 1 L/acre each application, at the V8 stage and VT stages (FIG. 4B).

Figure 4C:
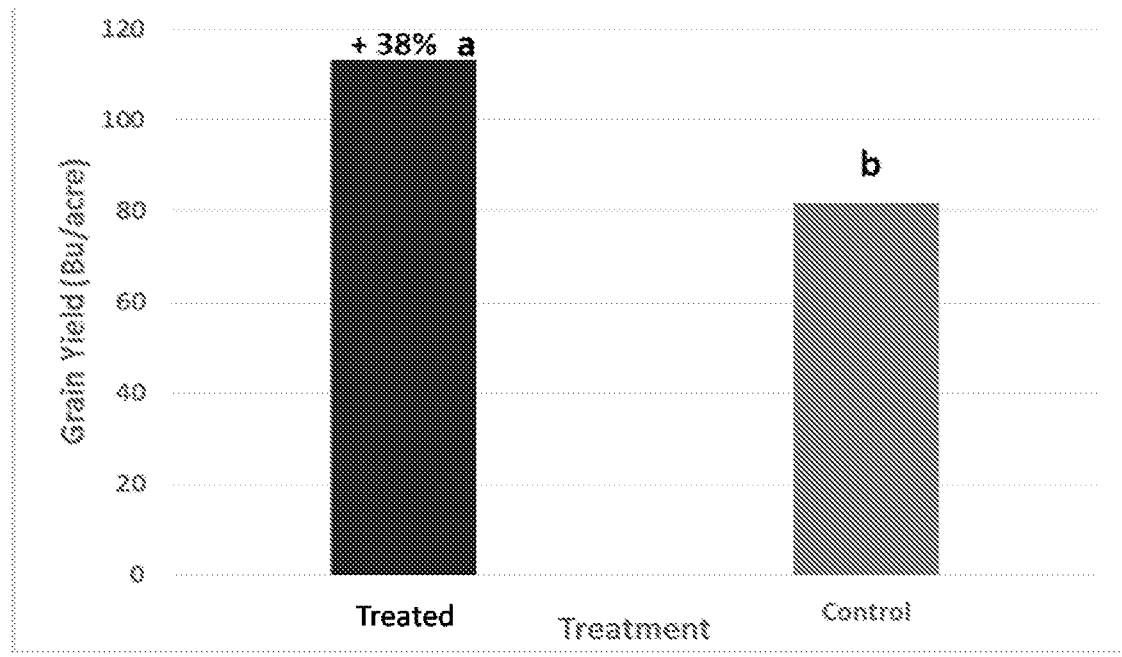

Trial C was also a randomized and replicated plot design trial in corn, performed under water stress conditions. In this study, the amount of irrigation was limited to 11 inches of water versus the appropriately watered plots that received 17 inches of irrigation. A single 1 L/acre treatment of microbial composition, delivered at stage V6 with 28% nitrogen fertilizer via drip irrigation (Treated), produced a 38% yield increase over plots treated with fertilizer alone (untreated Check). The harvest increase observed with microbial composition treatment represents a potential of 31 Bu/acre higher yield (FIG. 4C).

Example 9

Treatment of Tomato with A1007

This example describes effect of A1007 microbial compositions on tomato crop yield. Treatment of tomato with the microbial composition showed a strong increase in final harvestable yield. All agronomic practices of fertilization, cultivation, weed control, and pest control, were identical and side-by-side for both the microbial composition-treated (Test) and control (Check) plots.

The microbial consortium A1007 (referred to in this example as "HYT A") was tested in a completely randomized, replicated plot greenhouse trial of an indeterminate tomato cultivar, comparing frequency and dose of microbial application and the impact on yield. In all cases, identical standard farmer practices were employed, including nutritional input, pollination, and pest control. Soil was pre-treated with HYT A (2 L/ha) plus HYT B (6 L/ha), with an additional dose at planting (HYT A 1 L/ha, HYT B 3 L/ha). During plant growth, treatment represented three replicates, each 30 sq. meter plots, with HYT A and HYT B applied by drip irrigation at three week intervals, with the first dose doubled (HYT A 2 L/ha, HYT B 4 L/ha) and subsequent doses at half that rate (HYT A 1 L/ha and HYT B 2 L/ha). Yield was measured at every fruit harvest over a six month harvest cycle.

Figure 5:
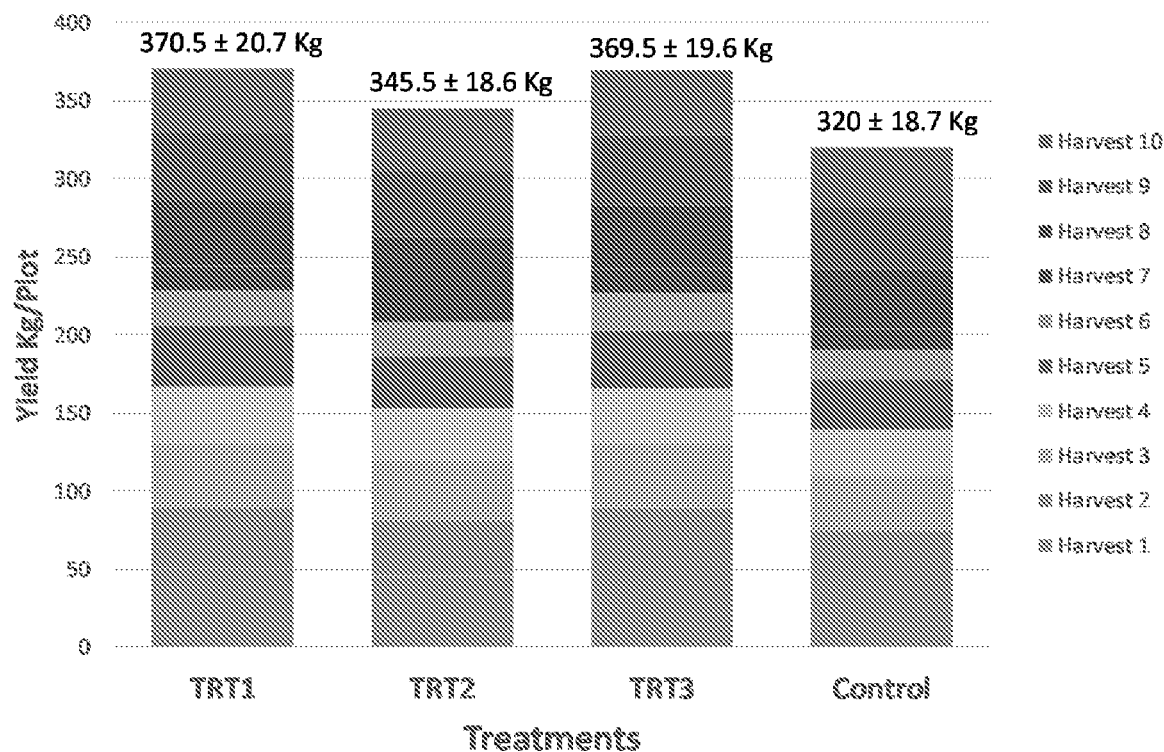
FIG. 5 is a graph showing yield in tomato plants treated with A1007 plus HYT B without activation (TRT1), A1007 plus HYT B at half-rate without activation (TRT2), A1007 plus HYT B with three day activation (TRT3), or control. For each treatment the different bands indicate harvests 1-10 (bottom to top).

Treatment 1 was not activated or pre-incubated prior to plant exposure, whereas Treatment 3 represents HYT A/HYT B that had been pre-incubated together, and activated, for three days prior to application. In this case, tomato yields for both non-activated and activated were nearly identical at 370 kg/plot and 369 kg/plot. Compared to the control (Treatment 4), this increased yield is about 50 kg/30 sq. meter plot (15% yield increase), which represents a 16,600 kg/ha potential boosted yield. Even half-rate of HYT A and HYT B (Treatment 2) raises overall productivity by 25 kg/plot or about 8% yield increase (FIG. 5).

Example 10

Increased Stress Tolerance in Potato

This example describes a representative method for obtaining increased potato tuber quality by treating with a microbial composition similar to A1007 and HYT B during growth under stressful field conditions.

Russet Burbank variety potato was grown under conventional conditions in a replicated plot trial (four replicates) and either treated (microbial composition plus HYT B at 1 L each per acre at planting, in furrow, followed by two foliar spray applications of HYT B at 1 L/acre at 55 days and again 85 days after planting) or untreated (control). Russet Burbank variety is prone to lower quality under water, heat, or nutrient stress. In this trial, the microbial composition and HYT B treatment enhanced tolerance to a stress-induced quality defect called hollow heart. Plots treated with microbial composition had an incidence of 1.68% of harvested tubers with hollow heart compared to the control with 8.35% hollow heart defects (Table 4).

TABLE 4

| Potato hollow heart quality defects | | |
| --- | --- | --- |
| Treatment | Yield (kg/acre) | Hollow Heart percentage |
| Untreated (control) | 32,181 | 8.35% |
| Microbial composition plus HYT B | 32,636 | 1.68%* |

*$p < 0.01$ compared to untreated

Example 11

Increased Nematode Tolerance in Potato

Large strip trials (0.12 ha/treatment) of the potato variety Nectar were planted in land with high incidence of potato cyst nematode (PCN) infestation. At the beginning of the trial, PCN egg and cyst counts in the soil at 8 multiple GPS sites per plot, from which 20 independent samples were taken and combined in an amalgamated sample at each location, representing initial PCN infection levels. These egg and cyst counts were repeated at the end of the trial at the same GPS location at harvest time to assess the impact of treatment on season-long PCN replication. Ten to 24 plants, depending on the site, per plot at each GPS location were harvested to measure yield proximal to specific PCN measurements. In addition, tubers from the entire 0.12 ha strip trial for each treatment was harvested for total plot yield. Five different treatments were compared, including A1007 ("HYT A") plus HYT B (once at planting and once at emergence) at a rate of 4 L/ha of HYT A and 2.5 L/ha HYT B, with or without an additional 4 L HYT D (twice, applied at planting and at emergence) or 1.5 kg/ha HYT C (twice, applied at planting and at emergence). Check plots in this study used the conventional farming practice of treating with the nematicide fosthiazate (nemathorin 10 G containing 10% w/w fosthiazate, 30 kg/ha) or the untreated control plot.

Figure 6A:
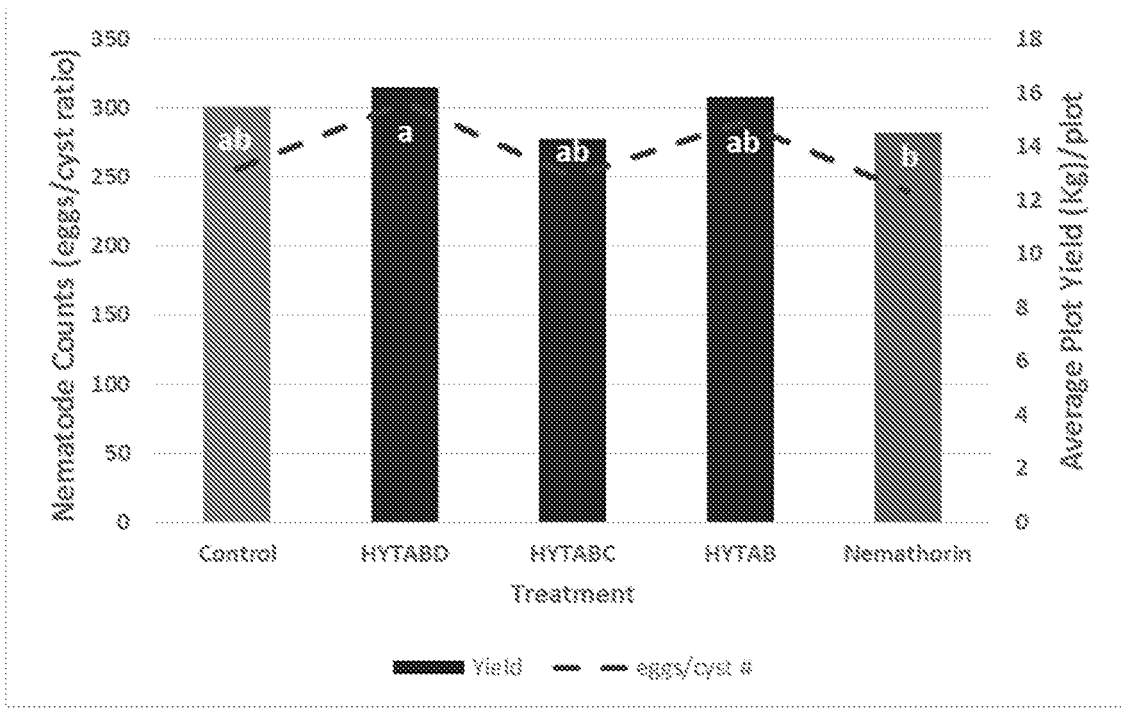
FIGS. 6A and 6B are graphs showing nematode prevalence (left axis—dotted line) and localized tuber yields (right axis—bars) after growth with treatments including HYT A (A1007) or nemathorin (FIG. 6A), and total plot potato yields after growth with the indicated treatments (FIG. 6B).
Figure 6B:
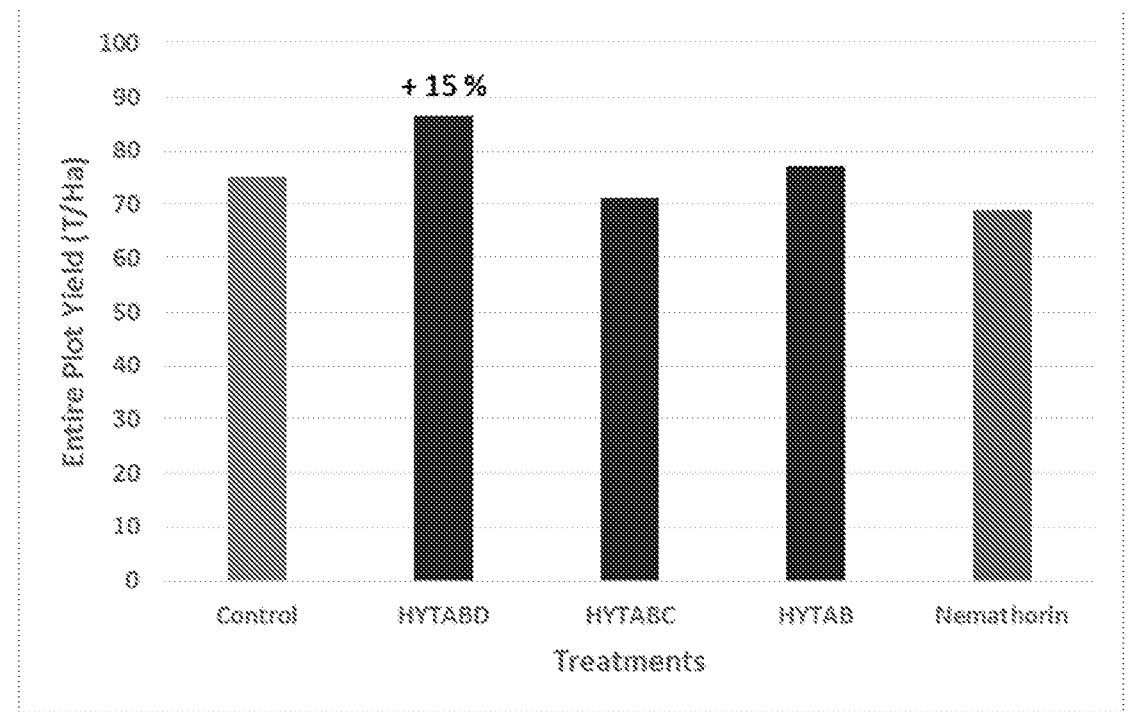

When assessed at the specific GPS locations, nemathorin treatment significantly reduced the nematode egg/cyst ratio counts compared to the other treatments (FIG. 6A). When total harvest from each treatment is compared, the treatment with HYT A-HYT B-HYT D combination produced 15% more yield than the untreated control and about 25% greater yield than nemathorin treatment (FIG. 6B). These results suggest that a combined HYT A-HYT B-HYT D treatment is not nematicidal, but can help plants remain productive in the presence of nematodes, for example by potentially supporting uptake of nutrients, thus maintaining plant health.

Example 12

Increased Plant Vigor in Model Plant Systems

Rapid plant-based functional assays can be used to quickly evaluate plant response to new microbial compositions. Using a cucumber vigor and plant growth assay, this example demonstrates that A1007 enhances the rate of plant leaf growth and expansion.

The microbial composition A1007 was diluted 1:2000 in a nutrient fertilizer media. After pre-germination of cucumber seedlings in nutrient-soaked rolled germination paper for four days, staged and synchronized plants were treated with the diluted mixture of liquid fertilizer and A1007. Plantlets were transplanted into prepared soilless growth medium pre-treated with fertilizer and A1007. As control treatments, either an equivalent amount of water added to nutrient media or a 1:2000 dilution of 0.2 µm filter-sterilized A1007 were compared. At least 18 plants of each treatment grown in pots, including control plants, were randomized in flats, and grown under defined growth conditions, controlling for temperature and light. After 17 days, the Leaf Area Index (LAI) of the first true leaf of each plant was measured. A second LAI measurement of the third true leaf was measured around day 28. The total plant wet weight was also recorded. The data was analyzed by One-way ANOVA (Analysis Of Variance) and with post-hoc Tukey test to compare samples within the experiment.

Figure 7:
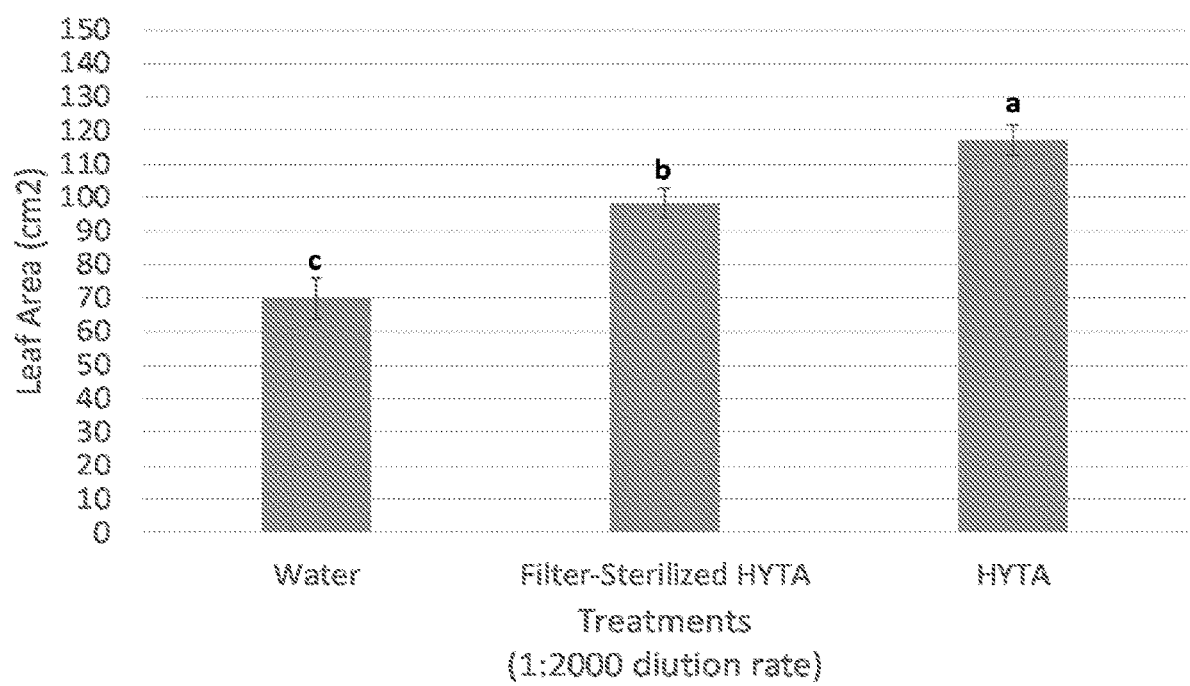
FIG. 7 is a graph of a cucumber vigor assay showing third leaf area index (LAI) on day 27 in plants treated with HYT A (A1007). Letters (a, b, c) indicate significant differences at p<0.05 by ANOVA analysis.

At day 17, the first leaf LAI ratings of the three treatments showed minor differences. By day 27, the enhanced growth of the third leaf (LAI) promoted by A1007 was significantly greater than that of either water or filter-sterilized A1007 controls (FIG. 7).

Example 13

Analysis of Microbes in A1007 by Microarray

This example describes microarray analysis of microbes present in A1007.

A 1 ml sample of well-mixed A1007 solution was utilized for genomic DNA preparation using PowerSoil® DNA isolation kit (Mo Bio Laboratories, Carlsbad, Calif.). The microbial community of A1007 was analyzed with the PhyloChip assay (Second Genome, South San Francisco, Calif.) using the isolated genomic DNA. A total of 578 Operational Taxonomic Units (OTUs) were identified from A1007 by this analysis. The data from the microarray analysis were used to select microbes for inclusion in the compositions described herein, in combination with the data described in Examples 2-4. In particular, the microarray analysis identified presence of *Streptomyces* spp. from A1007, which was selected for inclusion in some of the microbial compositions described herein.

Listing of Various Embodiments

In addition to, or as an alternative to the above, the following embodiments are described:

Embodiment 1 is directed to a composition comprising the microbes in ATCC deposit PTA-122728 (A1007).

Embodiment 2 is directed to a composition comprising five or more microbial species selected from *Bacillus* spp., *Lactobacillus* spp., *Clostridium* spp., *Virgibacillus* spp., *Brevibacillus* spp., *Paenibacillus* spp., *Oceanobacillus* spp., *Lysinibacillus* spp., *Acetobacter* spp., *Rummeliibacillus* spp., and *Candida* spp.

Embodiment 3 is directed to a composition comprising ten or more microbial species selected from *Bacillus* spp., *Lactobacillus* spp., *Clostridium* spp., *Virgibacillus* spp., *Brevibacillus* spp., *Paenibacillus* spp., *Oceanobacillus* spp., *Lysinibacillus* spp., *Acetobacter* spp., *Rummeliibacillus* spp., and *Candida* spp.

Embodiment 4 is directed to a microbial composition comprising microbial species selected from each of *Bacillus* spp., *Lactobacillus* spp., *Clostridium* spp., *Virgibacillus* spp., *Brevibacillus* spp., *Paenibacillus* spp., *Oceanobacillus* spp., *Lysinibacillus* spp., *Acetobacter* spp., *Rummeliibacillus* spp., and *Candida* spp.

Embodiment 5 is directed to a microbial composition comprising the microbial species of any one of embodiments 2 to 4, further comprising microbial species from *Streptomyces* spp.

Embodiment 6 is directed to a microbial composition comprising five or more microbial species selected from *Bacillus* spp., *Lactobacillus* spp., *Clostridium* spp., *Streptomyces* spp., *Virgibacillus* spp., *Brevibacillus* spp., *Paenibacillus* spp., *Oceanobacillus* spp., *Lysinibacillus* spp., *Acetobacter* spp., *Rummeliibacillus* spp., and *Candida* spp.

Embodiment 7 is directed to a microbial composition comprising ten or more microbial species selected from *Bacillus* spp., *Lactobacillus* spp., *Clostridium* spp., *Streptomyces* spp., *Virgibacillus* spp., *Brevibacillus* spp., *Paenibacillus* spp., *Oceanobacillus* spp., *Lysinibacillus* spp., *Acetobacter* spp., *Rummeliibacillus* spp., and *Candida* spp.

Embodiment 8 is directed to a microbial composition comprising microbial species selected from each of *Bacillus* spp., *Lactobacillus* spp., *Clostridium* spp., *Streptomyces* spp., *Virgibacillus* spp., *Brevibacillus* spp., *Paenibacillus* spp., *Oceanobacillus* spp., *Lysinibacillus* spp., *Acetobacter* spp., *Rummeliibacillus* spp., and *Candida* spp.

Embodiment 9 is directed to a composition of any one of embodiments 2 to 8, wherein the *Bacillus* spp. comprises one or more of *Bacillus flexus*, *Bacillus circulans*, *Bacillus subtilis*, *Bacillus pumilus*, *Bacillus licheniformis*, *Bacillus amyloliquefaciens*, *Bacillus pocheonensis*, and *Bacillus clausii*.

Embodiment 10 is directed to a composition of any one of embodiments 2 to 9, wherein the *Lactobacillus* spp. comprises *Lactobacillus vini* and/or *Lactobacillus buchneri*.

Embodiment 11 is directed to a composition of any one of embodiments 2 to 10, wherein the *Clostridium* spp. comprises one or more of *Clostridium nitrophenolcium*, *Clostridium beijerinckii*, and *Clostridium pasteurianum*.

Embodiment 12 is directed to a composition of any one of embodiments 2 to 11, wherein the *Paenibacillus* spp. comprises one or more of *Paenibacillus brevis*, *Paenibacillus cookii*, *Paenibacillus lautus*, *Paenibacillus*, *chibensis*, *Paenibacillus anaericanus*, and *Paenibacillus agaridevorans*.

Embodiment 13 is directed to a composition of any one of embodiments 2 to 12, wherein the *Oceanobacillus* spp. comprises *Oceanobacillus oncorhynchi* subsp. *incaldanensis*.

Embodiment 14 is directed to a composition of any one of embodiments 2 to 13, wherein the *Lysinibacillus* spp. comprises *Lysinibacillus xylanilyticus*.

Embodiment 15 is directed to a composition of any one of embodiments 2 to 14, wherein the *Acetobacter* spp. comprises *Acetobacter pasteurianum*.

Embodiment 16 is directed to a composition of any one of embodiments 2 to 15, wherein the *Rummeliibacillus* spp. comprises *Rummeliibacillus pycnus*.

Embodiment 17 is directed to composition of any one of embodiments 2 to 16, wherein the *Candida* spp. comprises *Candida ethanolica*.

Embodiment 18 is directed to a composition of any one of embodiments 2 to 17, further comprising one or more of *Bacillus subterraneus, Bacillus oceanisediminis, Bacillus firmus, Virgibacillus halophilus, Brevibacillus brevis, Paenibacillus validus, Paenibacillus timonensis, Paenibacillus cineris, Paenibacillus rhizoospherae, Paenibacillus favisporus, Clostridium tyrobutyricum, Clostridium sphenoides, Lysinibacillus fusiformis,* and *Rummeliibacillus stabekisii*.

Embodiment 19 is directed to the composition of any one of embodiments 2 to 18, further comprising one or more of *Azotobacter* spp. and *Rhizobium* spp.

Embodiment 20 is directed to the composition of embodiment 19, wherein the *Azotobacter* spp. comprises *Azotobacter vinelandii* and/or *Azotobacter chroococcum* or the *Rhizobium* spp. comprises *Rhizobium japonicus* and/or *Rhizobium leguminosarum*.

Embodiment 21 is directed to a composition of any one of embodiments 2 to 20, further comprising one or more of chitin, chitosan, glucosamine, and amino acids.

Embodiment 22 is directed to a method comprising mixing a chitin-containing biological source with the composition of any one of embodiments 1 to 21 to form a mixture; fermenting the mixture; and separating the fermented mixture into solid, aqueous, and lipid fractions.

Embodiment 23 is directed to the method of embodiment 22, wherein the chitin-containing biological source comprises a marine animal or marine animal by-product, an insect, or a fungus.

Embodiment 24 is directed to the method of embodiment 23, wherein the marine animal is a marine arthropod.

Embodiment 25 is directed to the method of embodiment 24, wherein the marine arthropod is shrimp, crab, or krill.

Embodiment 26 is directed to the aqueous fraction made by the method of any one of embodiments 22 to 25.

Embodiment 27 is directed to the solid fraction made by the method of any one of embodiments 22 to 24.

Embodiment 28 is directed to a method comprising contacting soil, plants, or plant parts with the composition of any one of embodiments 1 to 21.

Embodiment 29 is directed to the method of embodiment 28, further comprising contacting the soil, plants, or plant parts with one or more of chitin, chitosan, glucosamine, and amino acids.

Embodiment 30 is directed to the method of embodiments 28 or 29, further comprising contacting the soil, plants, or plant parts with the aqueous fraction of embodiment 26 and/or the solid fraction of embodiment 27.

Embodiment 31 is directed to the method of any one of embodiments 28 to 30, further comprising contacting the soil, plants, or plant parts with a liquid fertilizer.

Embodiment 32 is directed to the method of any one of embodiments 28 to 31, further comprising contacting the soil, plants, or plant parts with one or more pesticides, one or more fungicides, one or more herbicides, one or more insecticides, one or more plant hormones, one or more plant elicitors, or combinations of two or more thereof.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method comprising:
mixing a chitin-containing biological source with a composition comprising cells of five or more microbial species selected from *Bacillus* spp., *Lactobacillus* spp., *Clostridium* spp., *Streptomyces* spp., *Virgibacillus* spp., *Brevibacillus* spp., *Paenibacillus* spp., *Oceanobacillus* spp., *Lysinibacillus* spp., *Acetobacter* spp., *Rummeliibacillus* spp., and *Candida* spp., wherein each of the five or more microbial species has a 16S rDNA sequence with at least 99% sequence identity to one of SEQ ID NOs: 1-17 to form a mixture;
fermenting the mixture; and
separating the fermented mixture into solid, aqueous, and lipid fractions.

2. The method of claim 1, wherein the chitin-containing biological source comprises a marine animal or marine animal by-product, an insect, or a fungus.

3. A method comprising contacting soil, plants, or plant parts with a composition comprising cells of five or more microbial species selected from *Bacillus* spp., *Lactobacillus* spp., *Clostridium* spp., *Streptomyces* spp., *Virgibacillus* spp., *Brevibacillus* spp., *Paenibacillus* spp., *Oceanobacillus* spp., *Lysinibacillus* spp., *Acetobacter* spp., *Rummeliibacillus* spp., and *Candida* spp., wherein each of the five or more microbial species has a 16S rDNA sequence with at least 99% sequence identity to one of SEQ ID NOs: 1-17.

4. The method of claim 3, further comprising contacting the soil, plants, or plant parts with:
one or more of chitin, chitosan, glucosamine, and amino acids;
a liquid fertilizer; and/or
one or more pesticides, one or more fungicides, one or more herbicides, one or more insecticides, one or more plant hormones, one or more plant elicitors, or combinations of two or more thereof.

5. The method of claim 1, wherein the composition comprises cells of ten or more microbial species selected from *Bacillus* spp., *Lactobacillus* spp., *Clostridium* spp., *Streptomyces* spp., *Virgibacillus* spp., *Brevibacillus* spp., *Paenibacillus* spp., *Oceanobacillus* spp., *Lysinibacillus* spp., *Acetobacter* spp., *Rummeliibacillus* spp., and *Candida* spp.

6. The method of claim 1, wherein the composition comprises cells of five or more microbial species having 16S rDNA sequences comprising any one of SEQ ID NOs: 1-17.

7. The method of claim 1, wherein the composition comprises cells of microbial species selected from each of

*Bacillus* spp., *Lactobacillus* spp., *Clostridium* spp., *Streptomyces* spp., *Virgibacillus* spp., *Brevibacillus* spp., *Paenibacillus* spp., *Oceanobacillus* spp., *Lysinibacillus* spp., *Acetobacter* spp., *Rummeliibacillus* spp., and *Candida* spp.

8. The method of claim 1, wherein:
the *Bacillus* spp. comprises one or more of *Bacillus flexus, Bacillus circulans, Bacillus subtilis, Bacillus pumilus, Bacillus licheniformis, Bacillus amyloliquefaciens, Bacillus pocheonensis*, and *Bacillus clausii*;
the *Lactobacillus* spp. comprises *Lactobacillus vini* and/or *Lactobacillus buchneri*;
the *Clostridium* spp. comprises one or more of *Clostridium nitrophenolicum, Clostridium beijerinckii*, and *Clostridium pasteurianum*;
the *Paenibacillus* spp. comprises one or more of *Paenibacillus brevis, Paenibacillus cookii, Paenibacillus lautus, Paenibacillus, chibensis, Paenibacillus anaericanus*, and *Paenibacillus agaridevorans*;
the *Oceanobacillus* spp. comprises *Oceanobacillus oncorhynchi* subsp. *incaldanensis*;
the *Lysinibacillus* spp. comprises *Lysinibacillus xylanilyticus*;
the *Acetobacter* spp. comprises *Acetobacter pasteurianum*;
the *Rummeliibacillus* spp. comprises *Rummeliibacillus pycnus*; and/or
the *Candida* spp. comprises *Candida ethanolica*.

9. The method of claim 1, wherein the composition further comprises cells of one or more of *Bacillus subterraneus, Bacillus oceanisediminis, Bacillus firmus, Virgibacillus halophilus, Brevibacillus brevis, Paenibacillus validus, Paenibacillus timonensis, Paenibacillus cineris, Paenibacillus rhizoospherae, Paenibacillus favisporus, Clostridium tyrobutyricum, Clostridium sphenoides, Lysinibacillus fusiformis*, and *Rummeliibacillus stabekisii*.

10. The method of claim 1, wherein the composition further comprises cells of one or more of *Azotobacter* spp. and *Rhizobium* spp.

11. The method of claim 10, wherein the *Azotobacter* spp. comprises *Azotobacter vinelandii* and/or *Azotobacter chroococcum* or the *Rhizobium* spp. comprises *Rhizobium japonicus* and/or *Rhizobium leguminosarum*.

12. The method of claim 3, wherein the composition comprises cells of ten or more microbial species selected from *Bacillus* spp., *Lactobacillus* spp., *Clostridium* spp., *Streptomyces* spp., *Virgibacillus* spp., *Brevibacillus* spp., *Paenibacillus* spp., *Oceanobacillus* spp., *Lysinibacillus* spp., *Acetobacter* spp., *Rummeliibacillus* spp., and *Candida* spp.

13. The method of claim 3, wherein the composition comprises cells of five or more microbial species having 16S rDNA sequences comprising any one of SEQ ID NOs: 1-17.

14. The method of claim 3, wherein the composition comprises cells of microbial species selected from each of *Bacillus* spp., *Lactobacillus* spp., *Clostridium* spp., *Streptomyces* spp., *Virgibacillus* spp., *Brevibacillus* spp., *Paenibacillus* spp., *Oceanobacillus* spp., *Lysinibacillus* spp., *Acetobacter* spp., *Rummeliibacillus* spp., and *Candida* spp.

15. The method of claim 3, wherein:
the *Bacillus* spp. comprises one or more of *Bacillus flexus, Bacillus circulans, Bacillus subtilis, Bacillus pumilus, Bacillus licheniformis, Bacillus amyloliquefaciens, Bacillus pocheonensis*, and *Bacillus clausii*;
the *Lactobacillus* spp. comprises *Lactobacillus vini* and/or *Lactobacillus buchneri*;
the *Clostridium* spp. comprises one or more of *Clostridium nitrophenolicum, Clostridium beijerinckii*, and *Clostridium pasteurianum*;
the *Paenibacillus* spp. comprises one or more of *Paenibacillus brevis, Paenibacillus cookii, Paenibacillus lautus, Paenibacillus, chibensis, Paenibacillus anaericanus*, and *Paenibacillus agaridevorans*;
the *Oceanobacillus* spp. comprises *Oceanobacillus oncorhynchi* subsp. *incaldanensis*;
the *Lysinibacillus* spp. comprises *Lysinibacillus xylanilyticus*;
the *Acetobacter* spp. comprises *Acetobacter pasteurianum*;
the *Rummeliibacillus* spp. comprises *Rummeliibacillus pycnus*; and/or
the *Candida* spp. comprises *Candida ethanolica*.

16. The method of claim 3, wherein the composition further comprises cells of one or more of *Bacillus subterraneus, Bacillus oceanisediminis, Bacillus firmus, Virgibacillus halophilus, Brevibacillus brevis, Paenibacillus validus, Paenibacillus timonensis, Paenibacillus cineris, Paenibacillus rhizoospherae, Paenibacillus favisporus, Clostridium tyrobutyricum, Clostridium sphenoides, Lysinibacillus fusiformis*, and *Rummeliibacillus stabekisii*.

17. The method of claim 3, wherein the composition further comprises cells of one or more of *Azotobacter* spp. and *Rhizobium* spp.

18. The method of claim 17, wherein the *Azotobacter* spp. comprises *Azotobacter vinelandii* and/or *Azotobacter chroococcum* or the *Rhizobium* spp. comprises *Rhizobium japonicus* and/or *Rhizobium leguminosarum*.

19. The method of claim 1, wherein the microbial composition comprises the microbes in ATCC deposit number PTA-122728.

20. The method of claim 3, wherein the microbial composition comprises the microbes in ATCC deposit number PTA-122728.

* * * * *

SEQUENCE LISTING

```
<160> NUMBER OF SEQ ID NOS: 17

<210> SEQ ID NO 1
<211> LENGTH: 1579
<212> TYPE: DNA
<213> ORGANISM: Lactobacillus sp.

<400> SEQUENCE: 1
tatgagagtt tgatcctggc tcaggatgaa cgctggcggc gtgcctaata catgcaagtc      60
gaacgagttc tcgttgatga tcggtgcttg caccgagatt caacatggaa cgagtggcgg     120
acgggtgagt aacacgtggg taacctgccc ttaagtgggg gataacattt ggaaacagat     180
gctaataccg catagatcca agaaccgcat ggttcttggc tgaaagatgg cgtaagctat     240
cgcttttgga tggacccgcg gcgtattagc tagttggtga ggtaacggct caccaaggcg     300
atgatacgta gccgaactga gaggttgatc ggccacattg ggactgagac acggcccaaa     360
ctcctacggg aggcagcagt agggaatctt ccacaatgga cgcaagtctg atggagcaac     420
gccgcgtgag tgaagaaggc tttcgggtcg taaaactctg ttgttggaga agaatggtcg     480
gcagagtaac tgttgtcggc gtgacggtat ccaaccagaa agccacggct aactacgtgc     540
cagcagccgc ggtaatacgt aggtggcaag cgttatccgg atttattggg cgtaaagcga     600
gcgcaggcgg ttttttaagt ctgatgtgaa agccctcggc ttaaccgagg aagcgcatcg     660
```

```
gaaactggga aacttgagtg cagaagagga cagtggaact ccatgtgtag cggtgaaatg    720
cgtagatata tggaagaaca ccagtggcga aggcggctgt ctggtctgta actgacgctg    780
aggctcgaaa gcatgggtag cgaacaggat tagataccct ggtagtccat gccgtaaacg    840
atgaatgcta ggtgttggag ggtttccgcc cttcagtgcc gcagctaacg cattaagcat    900
tccgcctggg gagtacgacc gcaaggttga aactcaaagg aattgacggg ggcccgcaca    960
agcggtggag catgtggttt aattcgaagc aacgcgaaga accttaccag gtcttgacat   1020
cttttgatca cctgagagat caggtttccc cttcggggc aaaatgacag gtggtgcatg    1080
gttgtcgtca gctcgtgtcg tgagatgttg ggttaagtcc gcaacgagc gcaacccttta    1140 tgactagttg ccagcattta gttgggcact ctagtaagac tgccggtgac aaaccggagg   1200
aaggtgggga tgacgtcaaa tcatcatgcc cctatgacc tgggctacac acgtgctaca    1260
atggatggta caacgagttg cgagaccgcg aggtcaagct aatctcttaa agccattctc   1320
agttcggact gtaggctgca actcgcctac acgaagtcgg aatcgctagt aatcgcggat   1380
cagcacgccg cggtgaatac gttcccgggc cttgtacaca ccgcccgtca ccatgaga    1440 gtttgtaaca cccgaagccg gtggcgtaac cctttaggg agcgagccgt ctaaggtggg   1500
acaaatgatt agggtgaagt cgtaacaagg tagccgtagg agaacctgcg gctggatcac    1560
ctcctttaag caccgatca                                                1579

<210> SEQ ID NO 2
<211> LENGTH: 1510
<212> TYPE: DNA
<213> ORGANISM: Clostridium beijerinckii

<400> SEQUENCE: 2
tattgagagt ttgatcctgg ctcaggacga acgctggcgg cgtgcttaac acatgcaagt     60
cgagcgatga agttccttcg ggaatggatt agcggcggac gggtgagtaa cacgtgggta    120
acctgcctca tagagggga tagcctttcg aaaggaagat taataccgca taagattgta    180
gtgccgcatg gcatagcaat taaggagta atccgctatg agatggaccc gcgtcgcatt    240
agctagttgg tgaggtaacg gctcaccaag gcgacgatgc gtagccgacc tgagagggtg    300
atcggccaca ttgggactga gacacggccc agactcctac gggaggcagc agtggggaat    360
attgcacaat gggggaaacc ctgatgcagc aacgccgcgt gagtgatgac ggtcttcgga    420
ttgtaaagct ctgtcttcag ggacgataat gacggtacct gaggaggaag ccacggctaa    480
ctacgtgcca gcagccgcgg taatacgtag gtggcaagcg ttgtccggat ttactgggcg    540
taaagggagc gtaggtggat atttaagtgg gatgtgaaat actcgggctt aacctgggtg    600
ctgcattcca aactggatat ctagagtgca ggagaggaaa gtagaattcc tagtgtagcg    660
gtgaaatgcg tagagattag gaagaatacc agtggcgaag gcgactttct ggactgtaac    720
tgacactgag gctcgaaagc gtggggagca acaggatta gatacctgg tagtccacgc      780 cgtaaacgat gaatactagg tgtaggggtt gtcatgacct ctgtgccgcc gctaacgcat    840
taagtattcc gcctgggag tacggtcgca agattaaaac tcaaaggaat tgacgggggc     900
ccgcacaagc agcggagcat gtggtttaat tcgaagcaac gcgaagaacc ttacctagac    960
ttgacatctc ctgaattacc cttaatcggg gaagcccttc ggggcaggaa gacaggtggt   1020
gcatggttgt cgtcagctcg tgtcgtgaga tgttgggtta gtcccgcaa cgagcgcaac    1080 ccttattgtt agttgctacc atttagttga gcactctagc gagactgccc gggttaaccg   1140
```

```
ggaggaaggt ggggatgacg tcaaatcatc atgcccctta tgtctagggc tacacacgtg    1200
ctacaatggc tggtacagag agatgctaaa ccgtgaggtg gagccaaact ttaaaaccag    1260
tctcagttcg gattgtaggc tgaaactcgc ctacatgaag ctggagttgc tagtaatcgc    1320
gaatcagaat gtcgcggtga atacgttccc gggccttgta cacaccgccc gtcacaccat    1380
gagagttggc aatacccaaa gttcgtgagc taacgcgcaa gcggggcagc gacctaaggt    1440
agggtcagcg attggggtga agtcgtaaca aggtagccgt aggagaacct gcggctggat    1500
cacctccttt                                                           1510

<210> SEQ ID NO 3
<211> LENGTH: 1485
<212> TYPE: DNA
<213> ORGANISM: Acetobacter pasteurianum

<400> SEQUENCE: 3
cctgagagtt tgatcctggc tcagagcgaa cgctggcggc atgcttaaca catgcaagtc      60
gcacgaaggt ttcggcctta gtggcggacg ggtgagtaac gcgtaggtat ctatccatgg     120
gtgggggata acactgggaa actggtgcta ataccgcatg acacctgagg gtcaaaggcg     180
caagtcgcct gtggaggagc ctgcgtttga ttagctagtt ggtggggtaa aggcctacca     240
aggcgatgat caatagctgg tttgagagga tgatcagcca cactgggact gagacacggc     300
ccagactcct acgggaggca gcagtgggga atattggaca tgggggcaa ccctgatcca     360 gcaatgccgc gtgtgtgaag aaggtcttcg gattgtaaag cactttcgac ggggacgatg     420
atgacggtac ccgtagaaga gccccggct aacttcgtgc cagcagccgc ggtaatacga     480 aggggctag cgttgctcgg aatgactggg cgtaaagggc gtgtaggcgg tttgtacagt     540
cagatgtgaa atccccggc ttaacctggg agctgcattt gatacgtgca gactagagtg     600
tgagagaggg ttgtggaatt cccagtgtag aggtgaaatt cgtagatatt gggaagaaca     660
ccggtggcga aggcggcaac ctggctcatt actgacgctg aggcgcgaaa gcgtggggag     720
caaacaggat tagataccct ggtagtccac gctgtaaacg atgtgtgcta gatgttgggt     780
gacttagtca ttcagtgtcg cagttaacgc gttaagcaca ccgcctgggg agtacggccg     840
caaggttgaa actcaaagga attgacgggg gcccgcacaa gcggtggagc atgtggttta     900
attcgaagca acgcgcagaa ccttaccagg gcttgaatgt agaggctgca agcagagatg     960
tttgtttccc gcaagggacc tctaacacag gtgctgcatg gctgtcgtca gctcgtgtcg    1020
tgagatgttg ggttaagtcc cgcaacgagc gcaaccccta tctttagttg ccatcaggtt    1080
gggctgggca ctctagagag actgccggtg acaagccgga ggaaggtggg gatgacgtca    1140
agtcctcatg gcccttatgt cctgggctac acacgtgcta caatggcggt gacagtggga    1200
agctaggtgg tgacaccatg ctgatctcta aaagccgtct cagttcggat tgcactctgc    1260
aactcgagtg catgaaggtg gaatcgctag taatcgcgga tcagcatgcc gcggtgaata    1320
cgttcccggg ccttgtacac accgcccgtc acaccatggg agttggtttg accttaagcc    1380
ggtgagcgaa ccgcaaggac gcagccgacc acggtcgggt cagcgactgg ggtgaagtcg    1440
taacaaggta gccgtagggg aacctgcggc tggatcacct ccttt                    1485

<210> SEQ ID NO 4
<211> LENGTH: 1571
<212> TYPE: DNA
<213> ORGANISM: Lactobacillus buchneri

<400> SEQUENCE: 4
```

```
atgagagttt gatcctggct caggacgaac gctggcggcg tgcctaatac atgcaagtcg      60
aacgcgtctc cgttaatgat tttaggtgct tgcacttgaa agatttaaca ttgagacgag     120
tggcgaactg gtgagtaaca cgtgggtaac ctgcccttga agtagggat aacacttgga      180 aacaggtgct aataccgtat aacaaccaaa accacctggt tttggtttaa aagacggctt     240
cggctgtcac tttaggatgg acccgcggcg tattagcttg ttggtaaggt aacggcctac     300
caaggcgatg atacgtagcc gacctgagag ggtaatcggc acattggga ctgagacacg      360 gcccaaactc ctacgggagg cagcagtagg gaatcttcca caatggacga aagtctgatg     420
gagcaacgcc gcgtgagtga tgaagggttt cggctcgtaa aactctgttg ttggagaaga     480
acaggtgtca gagtaactgt tgacatcttg acggtatcca accagaaagc cacggctaac     540
tacgtgccag cagccgcggt aatacgtagg tggcaagcgt tgtccggatt tattgggcgt     600
aaagcgagcg caggcggttt tttaggtctg atgtgaaagc cttcggctta accggagaag     660
tgcatcggaa accgggagac ttgagtgcag aagaggacag tggaactcca tgtgtagcgg     720
tgaaatgcgt agatatatgg aagaacacca gtggcgaagg cggctgtctg gtctgtaact     780
gacgctgagg ctcgaaagca tgggtagcga acaggattag ataccctggt agtccatgcc     840
gtaaacgatg agtgctaagt gttggagggt ttccgcccct cagtgctgca gctaacgcat     900
taagcactcc gcctggggag tacgaccgca aggttgaaac tcaaaggaat tgacggggc      960 ccgcacaagc ggtggagcat gtggtttaat tcgatgctac gcgaagaacc ttaccaggtc    1020
ttgacatctt ctgccaactt aagagattag gcgttccctt cggggacaga atgacaggtg    1080
gtgcatggtt gtcgtcagct cgtgtcgtga gatgttgggt taagtcccgc aacgagcgca    1140
acccttattg ttagttgcca gcattcagtt gggcactcta gcaagactgc cggtgacaaa    1200
ccggaggaag gtgggatga cgtcaaatca tcatgcccct tatgacctgg gctacacacg     1260
tgctacaatg gacggtacaa cgagtcgcga accgcgagg tcaagctaat ctcttaaagc     1320
cgttctcagt tcggattgta ggctgcaact cgcctacatg aagttggaat cgctagtaat    1380
cgtggatcag catgccacgg tgaatacgtt cccgggcctt gtacacaccg cccgtcacac    1440
catgagagtt tgtaacaccc aaagccggtg aggtaacctt cggggaccag ccgtctaagg    1500
tggggcagat gattagggtg aagtcgtaac aaggtagccg taggagaacc tgcggctgga    1560
tcacctcctt t                                                          1571

<210> SEQ ID NO 5
<211> LENGTH: 1548
<212> TYPE: DNA
<213> ORGANISM: Bacillus subtilis

<400> SEQUENCE: 5
atcggagagt ttgatcctgg ctcaggacga acgctggcgg cgtgcctaat acatgcaagt      60
cgagcggaca gatgggagct tgctccctga tgttagcggc ggacgggtga gtaacacgtg     120
ggtaacctgc ctgtaagact gggataactc cgggaaaccg gggctaatac cggatggttg     180
tttgaaccgc atggttcaaa cataaaaggt ggcttcggct accacttaca gatggacccg     240
cggcgcatta gctagttggt gaggtaacgg ctcaccaagg caacgatgcg tagccgacct     300
gagagggtga tcggccacac tgggactgag acacggccca gactcctacg ggaggcagca     360
gtagggaatc ttccgcaatg gacgaaagtc tgacggagca acgccgcgtg agtgatgaag     420
gttttcggat cgtaaagctc tgttgttagg gaagaacaag taccgttcga ataggggcggt    480
```

```
accttgacgg tacctaacca gaaagccacg gctaactacg tgccagcagc cgcggtaata    540
cgtaggtggc aagcgttgtc cggaattatt gggcgtaaag ggctcgcagg cggtttctta    600
agtctgatgt gaaagccccc ggctcaaccg ggagggtca ttggaaactg ggaacttga     660
gtgcagaaga ggagagtgga attccacgtg tagcggtgaa atgcgtagag atgtggagga    720
acaccagtgg cgaaggcgac tctctggtct gtaactgacg ctgaggagcg aaagcgtggg    780
gagcgaacag gattagatac cctggtagtc cacgccgtaa acgatgagtg ctaagtgtta    840
gggggtttcc gccccttagt gctgcagcta acgcattaag cactccgcct ggggagtacg    900
gtcgcaagac tgaaactcaa aggaattgac ggggcccgc acaagcggtg gagcatgtgg     960
tttaattcga agcaacgcga gaaccttac caggtcttga catcctctga caatcctaga   1020
gataggacgt ccccttcggg ggcagagtga caggtggtgc atggttgtcg tcagctcgtg   1080
tcgtgagatg ttgggttaag tcccgcaacg agcgcaaccc ttgatcttag ttgccagcat   1140
tcagttgggc actctaaggt gactgccggt gacaaaccgg aggaaggtgg ggatgacgtc   1200
aaatcatcat gccccttatg acctgggcta cacacgtgct acaatggaca gaacaaaggg   1260
cagcgaaacc gcgaggttaa gccaatccca caaatctgtt ctcagttcgg atcgcagtct   1320
gcaactcgac tgcgtgaagc tggaatcgct agtaatcgcg gatcagcatg ccgcggtgaa   1380
tacgttcccg ggccttgtac acaccgcccg tcacaccacg agagtttgta acacccgaag   1440
tcggtgaggt aacctttag gagccagccg ccgaaggtgg gacagatgat tgggtgaag    1500
tcgtaacaag gtagccgtat cggaaggtgc ggctggatca cctcctttt              1548
```

<210> SEQ ID NO 6
<211> LENGTH: 1552
<212> TYPE: DNA
<213> ORGANISM: Paenibacillus cookii

<400> SEQUENCE: 6

```
cttggagagt ttgatcctgg ctcaggacga acgctggcgg cgtgcctaat acatgcaagt     60
cgagcggagt tgatggggag cttgctctcc tgagacttag cggcggacgg gtgagtaaca    120
cgtaggcaac ctgcccgtaa gaccgggata actaccggaa acgtagcta ataccggata    180
atttatcgct tcgcatggag cggtaatgaa agacggagca atctgtcact tacggatggg    240
cctgcggcgc attagctagt tggtgaggta acggctcacc aaggcgacga tgcgtagccg    300
acctgagagg gtgaacggcc acactgggac tgagacacgg cccagactcc tacgggaggc    360
agcagtaggg aatcttccgc aatgggcgaa agcctgacgg agcaacgccg cgtgagtgat    420
gaaggttttc ggatcgtaaa gctctgttgc agggaagaa cgtcgggtag agtaactgct    480
atccgagtga cggtacctga aagaaagcc cggctaact acgtgccagc agccgcggta    540
atacgtaggg ggcaagcgtt gtccggaatt attgggcgta agcgcgcgc aggcggtcac    600
ttaagtctgg tgtttaaggc tagggctcaa ctctagttcg cactggaaac tgggtgactt    660
gagtgcagaa gaggaaagtg gaattccacg tgtagcggtg aaatgcgtag agatgtggag    720
gaacaccagt ggcgaaggcg actttctggg ctgtaactga cgctgaggcg cgaaagcgtg    780
gggagcaaac aggattagat accctggtag tccacgccgt aaacgatgaa tgctaggtgt    840
tagggtttc gataccccttg gtgccgaagt taacacatta gcattccgc ctggggagta    900
cggtcgcaag actgaaactc aaaggaattg acggggaccc gcacaagcag tggagtatgt    960
ggtttaattc gaagcaacgc gaagaacctt accaggtctt gacatccctc tgaatcctct   1020
agagatagag gcggccttcg ggacagagga gacaggtggt gcatggttgt cgtcagctcg   1080
```

```
tgtcgtgaga tgttgggtta agtcccgcaa cgagcgcaac ccttgattt agttgccagc    1140 acattaaggt gggcactcta gaatgactgc cggtgacaaa ccggaggaag gcggggatga    1200
cgtcaaatca tcatgcccct tatgacctgg gctacacacg tactacaatg gccagtacaa    1260
cgggaagcga agtcgcgaga cggagccaat cctatcaaag ctggtctcag ttcggattgc    1320
aggctgcaac ccgcctgcat gaagtcggaa ttgctagtaa tcgcggatca gcatgccgcg    1380
gtgaatacgt tcccgggtct tgtacacacc gcccgtcaca ccacgagagt ttacaacacc    1440
cgaagtcggt ggggtaaccg caaggagcca gccgccgaag gtggggtaga tgattggggt    1500
gaagtcgtaa caaggtagcc gtatcggaag gtgcggctgg atcacctcct tt           1552

<210> SEQ ID NO 7
<211> LENGTH: 1554
<212> TYPE: DNA
<213> ORGANISM: Lactobacillus vini

<400> SEQUENCE: 7
aatgagagtt tgatcctggc tcaggacgaa cgctggcggc gtgcctaata catgcaagtc      60
gaacgagact ttttatttga tgcttgcatc ttttaaaaag ttgagtggcg aacgggtgag     120
taacacgtgg gtaacctgcc ttaaagtggg ggataacact tggaaacagg tgctaatacc     180
gcataaccat caaaaccgcc tggttttgat gttaaagatg gttctgctat cgctttaaga     240
tggacccgcg gcgtattagc tagttggtga ggtaacggct taccaaggca atgatacgta     300
gccgaactga gaggttgatc ggccacattg ggactgagac acggcccaaa ctcctacggg     360
aggcagcagt agggaatctt tcacaatgga cgaaagtctg atggagcaac gccgcgtgag     420
tgaagaaggt tttcggatcg taaaactctg ttgtcagaga agaacgtgtg tgagagtaac     480
tgttcacgca gtgacggtat ctgaccagaa agtcacggct aactacgtgc cagcagccgc     540
ggtaatacgt aggtggcaag cgttgtccgg atttattggg cgtaaaggga acgcaggcgg     600
tcttttaagt ctgatgtgaa agccttcggc ttaaccgaag tcgggcattg gaaactggga     660
gacttgagtg cagaagagga gagtggaact ccatgtgtag cggtgaaatg cgtagatata     720
tggaagaaca ccagtggcga aagcggctct ctggtctgta actgacgctg aggttcgaaa     780
gcgtgggtag caaacaggat tagataccct ggtagtccac gccgtaaacg atgaatgcta     840
agtgttggag ggtttccgcc cttcagtgcc gcagctaacg cattaagcat tccgcctggg     900
gagtacgatc gcaagattga aactcaaagg aattgacggg ggcccgcaca agcggtggag     960
catgtggttt aattcgaagc aacgcgaaga accttaccag gtcttgacat cttttgctaa    1020
cctgagagat caggtgttcc cttcggggac aaaatgacag gtggtgcatg gttgtcgtca    1080
gctcgtgtcg tgagatgttg ggttaagtcc cgcaacgagc gcaacccta ttgttagttg     1140 ccagcattta gttgggcact ctaacgagac tgccggtgac aaaccggagg aaggtgggga    1200
tgacgtcaaa tcatcatgcc ccttatgacc tgggctacac acgtgctaca atggacggta    1260
caacgagtcg caagaccgcg aggtcaagct aatctctgaa aaccgttctc agttcggatt    1320
gcaggctgca actcgcctgc atgaagtcgg aatcgctagt aatcgcggat cagcatgccg    1380
cggtgaatac gttcccgggc cttgtacaca ccgcccgtca ccatgagagt ttgtaacac    1440 cccaaagccg gtggggtaac ctttgggagc cagccgtcta aggtgggaca gatgattggg    1500
gtgaagtcgt aacaaggtag ccgtaggaga acctgcggct ggatcacctc cttt         1554

<210> SEQ ID NO 8
```

```
<211> LENGTH: 1553
<212> TYPE: DNA
<213> ORGANISM: Paenibacillus lautus

<400> SEQUENCE: 8
attggagagt tgatcctgg ctcaggacga acgctggcgg cgtgcctaat acatgcaagt      60
cgagcggact tgatggagtg cttgcactcc tgaaggttag cggcggacgg gtgagtaaca     120
cgtaggcaac ctgccctcaa gactgggata actaccggaa acgtagcta ataccggata     180
atttattttg cagcattgtg aaataatgaa aggcggagca atctgtcact tgaggatggg    240
cctgcggcgc attagctagt tggtggggta acggcccacc aaggcgacga tgcgtagccg    300
acctgagagg gtgaacggcc acactgggac tgagacacg cccagactcc tacgggaggc    360
agcagtaggg aatcttccgc aatgggcgaa agcctgacgg agcaacgccg cgtgagtgat    420
gaaggttttc ggatcgtaaa gctctgttgc caaggaagaa cgtcttctag agtaactgct    480
aggagagtga cggtacttga aagaaagcc ccggctaact acgtgccagc agccgcggta    540
atacgtaggg ggcaagcgtt gtccggaatt attgggcgta aagcgcgcgc aggcggttct    600
ttaagtctgg tgtttaaacc cgaggctcaa cttcgggtcg cactggaaac tgggaactt    660
gagtgcagaa gaggagagtg gaattccacg tgtagcggtg aaatgcgtag atatgtggag    720
gaacaccagt ggcgaaggcg actctctggg ctgtaactga cgctgaggcg cgaaagcgtg    780
gggagcaaac aggattagat accctggtag tccacgccgt aaacgatgaa tgctaggtgt    840
taggggtttc gataccttg gtgccgaagt taacacatta gcattccgc ctggggagta     900
cggtcgcaag actgaaactc aaaggaattg acggggaccc gcacaagcag tggagtatgt    960
ggtttaattc gaagcaacgc gaagaacctt accaagtctt gacatccctc tgaatcctct   1020
agagatagag gcgccttcg ggacagaggt gacaggtggt gcatggttgt cgtcagctcg    1080
tgtcgtgaga tgttgggtta agtcccgcaa cgagcgcaac ccttgattt agttgccagc    1140
acttcgggtg gcactctag aatgactgcc ggtgacaaac cggaggaagg cggggatgac    1200
gtcaaatcat catgccccct tatgacttggg ctacacacgt actacaatgg ctggtacaac   1260
gggaagcgaa gccgcgaggt ggagccaatc ctataaaagc cagtctcagt tcggattgca    1320
ggctgcaact cgcctgcatg aagtcggaat tgctagtaat cgcggatcag catgccgcgg    1380
tgaatacgtt cccgggtctt gtacacaccg cccgtcacac cacgagagtt tacaacaccc    1440
gaagtcggtg gggtaaccct tagggagcc agccgccgaa ggtggggtag atgattgggg    1500
tgaagtcgta acaaggtagc cgtatcggaa ggtgcggctg gatcacctcc ttt          1553

<210> SEQ ID NO 9
<211> LENGTH: 1561
<212> TYPE: DNA
<213> ORGANISM: Oceanobacillus oncorhynchi subsp. incaldanensis

<400> SEQUENCE: 9
ttatggagag tttgatcttg gctcaggacg aacgctggcg gcgtgcctaa tacatgcaag     60
tcgagcgcgg gaagcgaacg gaactcttcg gagggaagtt cgtggaacga gcggcggacg    120
ggtgagtaac acgtaggcaa cctgcctgta agactgggat aactcgcgga aacgcgagct    180
aataccggat aacactttct atcacctgat ggaaagttga aggcggctt tgctgtcac     240
ttacagatgg gcctgcggcg cattagctag ttggtgaggt aacggctcac caaggcgacg    300
atgcgtagcc gacctgagag ggtgatcggc cacactggga ctgagacacg cccagactc    360
ctacgggagg cagcagtagg gaatcttccg caatggacga aagtctgacg gagcaacgcc    420
```

```
gcgtgagtga tgaaggtttt cggatcgtaa aactctgttg tcagggaaga caagtacga      480 tagtaactga tcgtaccttg acggtacctg accagaaagc cacggctaac tacgtgccag     540
cagccgcggt aatacgtagg tggcaagcgt tgtccggaat tattgggcgt aaagcgctcg     600
caggcggttc tttaagtctg atgtgaaatc ttgcggctca accgcaaacg tgcattggaa     660
actggaggac ttgagtgcag aagaggagag tggaattcca cgtgtagcgg tgaaatgcgt     720
agagatgtgg aggaacacca gtggcgaagg cgactctctg gtctgtaact gacgctgagg     780
agcgaaagcg tggggagcga acaggattag ataccctggt agtccacgcc gtaaacgatg     840
agtgctaggt gttagggggt ttccgcccct tagtgctgaa gttaacgcat taagcactcc     900
gcctggggag tacggccgca aggctgaaac tcaaaagaat tgacgggggac ccgcacaagc    960 ggtggagcat gtggtttaat tcgaagcaac gcgaagaacc ttaccaggtc ttgacatcct     1020
ttgaccgctc tagagataga gttttccctt cggggacaaa gtgacaggtg gtgcatggtt     1080
gtcgtcagct cgtgtcgtga gatgttgggt taagtcccgc aacgagcgca accctaatc      1140 ttagttgcca gcatttagtt gggcactcta aggtgactgc cggtgacaaa ccggaggaag     1200
gtggggatga cgtcaaatca tcatgcccct tatgacctgg gctacacacg tgctacaatg     1260
gacggaacaa agggaagcga acccgcgagg tccagcaaat cccataaaac cgttctcagt     1320
tcggattgca ggctgcaact cgcctgcatg aagccggaat cgctagtaat cgcggatcag     1380
catgccgcgg tgaatacgtt cccgggtctt gtacacaccg cccgtcacac cacgagagtt     1440
cgtaacaccc gaagtcggtg aggtaacctt ttggagccag ccgccgaagg tgggacgaat     1500
gattggggtg aagtcgtaac aaggtagccg tatcggaagg tgcggctgga tcacctcctt     1560
t                                                                    1561

<210> SEQ ID NO 10
<211> LENGTH: 1548
<212> TYPE: DNA
<213> ORGANISM: Bacillus amyloliquefaciens

<400> SEQUENCE: 10
atcggagagt ttgatcctgg ctcaggacga acgctggcgg cgtgcctaat acatgcaagt      60
cgagcggaca gatgggagct tgctccctga tgttagcggc ggacgggtga gtaacacgtg     120
ggtaacctgc ctgtaagact gggataactc cgggaaaccg gggctaatac cggatggttg     180
tctgaaccgc atggttcaga cataaaaggt ggcttcggct accacttaca gatggacccg     240
cggcgcatta gctagttggt gaggtaacgg ctcaccaagg cgacgatgcg tagccgacct     300
gagagggtga tcggccacac tgggactgag acacggccca gactcctacg ggaggcagca     360
gtagggaatc ttccgcaatg gacgaaagtc tgacggagca acgccgcgtg agtgatgaag     420
gttttcggat cgtaaagctc tgttgttagg gaagaacaag tgccgttcaa atagggcggc     480
accttgacgg tacctaacca gaaagccacg gctaactacg tgccagcagc cgcggtaata     540
cgtaggtggc aagcgttgtc cggaattatt gggcgtaaag ggctcgcagg cggtttctta     600
agtctgatgt gaaagccccc ggctcaaccg ggagggtca ttggaaactg ggaacttga      660 gtgcagaaga ggagagtgga attccacgtg tagcggtgaa atgcgtagag atgtggagga     720
acaccagtgg cgaaggcgac tctctggtct gtaactgacg ctgaggagcg aaagcgtggg     780
gagcgaacag gattagatac cctggtagtc cacgccgtaa acgatgagtg ctaagtgtta     840
gggggtttcc gccccttagt gctgcagcta acgcattaag cactccgcct ggggagtacg     900
```

| | |
|---|---|
| gtcgcaagac tgaaactcaa aggaattgac gggggcccgc acaagcggtg gagcatgtgg | 960 |
| tttaattcga agcaacgcga agaaccttac caggtcttga catcctctga caatcctaga | 1020 |
| gataggacgt ccccttcggg ggcagagtga caggtggtgc atggttgtcg tcagctcgtg | 1080 |
| tcgtgagatg ttgggttaag tcccgcaacg agcgcaaccc ttgatcttag ttgccagcat | 1140 |
| tcagttgggc actctaaggt gactgccggt gacaaaccgg aggaaggtgg ggatgacgtc | 1200 |
| aaatcatcat gccccttatg acctgggcta cacacgtgct acaatggaca gaacaaaggg | 1260 |
| cagcgaaacc gcgaggttaa gccaatccca caaatctgtt ctcagttcgg atcgcagtct | 1320 |
| gcaactcgac tgcgtgaagc tggaatcgct agtaatcgcg gatcagcatg ccgcggtgaa | 1380 |
| tacgttcccg ggccttgtac acaccgcccg tcacaccacg agagtttgta acacccgaag | 1440 |
| tcggtgaggt aacctttatg gagccagccg ccgaaggtgg gacagatgat tggggtgaag | 1500 |
| tcgtaacaag gtagccgtat cggaaggtgc ggctggatca cctcctttt | 1548 |

<210> SEQ ID NO 11
<211> LENGTH: 1547
<212> TYPE: DNA
<213> ORGANISM: Bacillus sp.

<400> SEQUENCE: 11

| | |
|---|---|
| attggagagt ttgatcctgg ctcaggacga acgctggcgg cgtgcctaat acatgcaagt | 60 |
| cgagcgaatc tgagggagct tgctcccaaa gattagcggc ggacgggtga gtaacacgtg | 120 |
| ggcaacctgc ctgtaagact gggataactc cgggaaaccg ggctaatacc ggataatat | 180 |
| ctatttatac atataattag attgaaagat ggttctgcta tcacttacag atgggcccgc | 240 |
| ggcgcattag ctagttggtg aggtaacggc tcaccaaggc gacgatgcgt agccgacctg | 300 |
| agagggtgat cggccacact gggactgaga cacggcccag actcctacgg gaggcagcag | 360 |
| tagggaatct tccgcaatgg acgaaagtct gacggagcaa cgccgcgtga gtgatgaagg | 420 |
| ttttcggatc gtaaaactct gttgttaggg aagaacaagt atcggagtaa ctgccggtac | 480 |
| cttgacggta cctaaccaga aagccacggc taactacgtg ccagcagccg cggtaatacg | 540 |
| taggtggcaa cgttgtccg gaattattgg gcgtaaagcg cgcgcaggcg gttccttaag | 600 |
| tctgatgtga aagcccacgg ctcaaccgtg gagggtcatt ggaaactggg gaacttgagt | 660 |
| gcagaagagg aaagtggaat tccaagtgta gcggtgaaat gcgtagagat ttggaggaac | 720 |
| accagtggcg aaggcgactt tctggtctgt aactgacgct gaggcgcgaa agcgtgggga | 780 |
| gcaaacagga ttagatacc tggtagtcca cgccgtaaac gatgagtgct aagtgttaga | 840 |
| gggtttccgc cctttagtgc tgcagcaaac gcattaagca ctccgcctgg ggagtacgac | 900 |
| cgcaaggttg aaactcaaag gaattgacgg gggcccgcac aagcggtgga gcatgtggtt | 960 |
| taattcgaag caacgcgaag aaccttacca ggtcttgaca tcctctgaca atcctagaga | 1020 |
| taggactttc cccttcgggg gacagagtga caggtggtgc atggttgtcg tcagctcgtg | 1080 |
| tcgtgagatg ttgggttaag tcccgcaacg agcgcaaccc ttgatcttag ttgccagcat | 1140 |
| ttagttgggc actctaaggt gactgccggt gacaaaccgg aggaaggtgg ggatgacgtc | 1200 |
| aaatcatcat gccccttatg acctgggcta cacacgtgct acaatggatg gtacaaaggg | 1260 |
| ctgcaagacc gcgaggttta gccaatccca taaaaccatt ctcagttcgg attgtaggct | 1320 |
| gcaactcgcc tacatgaagc cggaatcgct agtaatcgcg gatcagcatg ccgcggtgaa | 1380 |
| tacgttcccg ggccttgtac acaccgcccg tcacaccacg agagtttgta acacccgaag | 1440 |
| tcggtggggt aacctttgg agccagccgc ctaaggtggg acagatgatt ggggtgaagt | 1500 |

```
                cgtaacaagg tagccgtatc ggaaggtgcg gctggatcac ctccttt          1547

<210> SEQ ID NO 12
<211> LENGTH: 1553
<212> TYPE: DNA
<213> ORGANISM: Paenibacillus chibensis

<400> SEQUENCE: 12
cttggagagt tgatcctgg ctcaggacga acgctggcgg cgtgcctaat acatgcaagt       60
cgagcggagt tgatgaggtg cttgcacctc tgatgcttag cggcggacgg gtgagtaaca      120
cgtaggtaac ctgcctgtaa gactgggata actaccggaa acgtagcta ataccggata       180 atttattttc tctcctgggg agataatgaa agacggagca atctgtcact tacagatggg      240
cctgcggcgc attagctagt tggtgaggta acggctcacc aaggcgacga tgcgtagccg      300
acctgagagg gtgaacggcc acactgggac tgagacacgg cccagactcc tacgggaggc      360
agcagtaggg aatcttccgc aatggacgaa agtctgacgg agcaacgccg cgtgagtgat      420
gaaggttttc ggatcgtaaa gctctgttgc agggaagaa cgtccggtag agtaactgct       480
accggagtga cggtacctga aagaaagcc ccggctaact acgtgccagc agccgcggta       540
atacgtaggg ggcaagcgtt gtccggaatt attgggcgta aagcgcgcgc aggcggtcac      600
ttaagtctgg tgtttaaggc caaggctcaa ccttggttcg cactggaaac tgggtgactt      660
gagtgcagaa gaggagagtg gaattccacg tgtagcggtg aaatgcgtag atatgtggag      720
gaacaccagt ggcgaaggcg actctctggg ctgtaactga cgctgaggcg cgaaagcgtg      780
gggagcaaac aggattagat accctggtag tccacgccgt aaacgatgaa tgctaggtgt      840
tagggggttc gataccctg gtgccgaagt aacacatta agcattccgc ctggggagta       900
cggtcgcaag actgaaactc aaaggaattg acggggaccc gcacaagcag tggagtatgt      960
ggtttaattc gaagcaacgc gaagaacctt accaagtctt gacatccctc tgaatcctct     1020
agagatagag gcggccttcg ggacagaggt gacaggtggt gcatggttgt cgtcagctcg     1080
tgtcgtgaga tgttgggtta agtcccgcaa cgagcgcaac ccttgatttt agttgccagc     1140
atttcggatg ggcactctag aatgactgcc ggtgacaaac cggaggaagg cggggatgac     1200
gtcaaatcat catgcccctt atgacttggg ctacacacgt actacaatgg ccagtacaac     1260
gggaagcgaa atcgcgagat ggagccaatc ctatcaaagc tggtctcagt tcggattgca     1320
ggctgcaacc cgcctgcatg aagtcggaat tgctagtaat cgcggatcag catgccgcgg     1380
tgaatacgtt cccgggtctt gtacacaccg cccgtcacac cacgagagtt tacaacaccc     1440
gaagtcggtg gggtaacccg caagggagcc agccgccgaa ggtggggtag atgattgggg     1500
tgaagtcgta acaaggtagc cgtatcggaa ggtgcggctg gatcacctcc ttt           1553

<210> SEQ ID NO 13
<211> LENGTH: 1550
<212> TYPE: DNA
<213> ORGANISM: Bacillus flexus

<400> SEQUENCE: 13
tcggagagtt tgatcctggc tcaggatgaa cgctggcggc gtgcctaata catgcaagtc       60
gagcgaactg attagaagct tgcttctatg acgttagcgg cggacgggtg agtaacacgt      120
gggcaacctg cctgtaagac tgggataact ccgggaaacc ggagctaata ccggataaca      180
ttttctcttg cataagagaa aattgaaaga tggtttcggc tatcacttac agatgggccc      240
```

```
gcggtgcatt agctagttgg tgaggtaacg gctcaccaag gcaacgatgc atagccgacc      300
tgagagggtg atcggccaca ctgggactga gacacggccc agactcctac gggaggcagc      360
agtagggaat cttccgcaat ggacgaaagt ctgacggagc aacgccgcgt gagtgatgaa      420
ggctttcggg tcgtaaaact ctgttgttag gaagaacaa gtacaagagt aactgcttgt       480
accttgacgg tacctaacca gaaagccacg gctaactacg tgccagcagc cgcggtaata      540
cgtaggtggc aagcgttatc cggaattatt gggcgtaaag cgcgcgcagg cggtttctta      600
agtctgatgt gaaagcccac ggctcaaccg tggagggtca ttggaaactg ggaacttga       660
gtgcagaaga gaaaagcgga attccacgtg tagcggtgaa atgcgtagag atgtggagga      720
acaccagtgg cgaaggcggc ttttggtct gtaactgacg ctgaggcgcg aaagcgtggg       780
gagcaaacag gattagatac cctggtagtc cacgccgtaa acgatgagtg ctaagtgtta      840
gagggtttcc gccctttagt gctgcagcta acgcattaag cactccgcct ggggagtacg      900
gtcgcaagac tgaaactcaa aggaattgac ggggcccgc acaagcggtg gagcatgtgg       960
tttaattcga agcaacgcga gaaccttac caggtcttga catcctctga caactctaga      1020
gatagagcgt tccccttcgg gggacagagt gacaggtggt gcatggttgt cgtcagctcg     1080
tgtcgtgaga tgttgggtta agtcccgcaa cgagcgcaac ccttgatctt agttgccagc     1140
atttagttgg gcactctaag gtgactgccg gtgacaaacc ggaggaaggt ggggatgacg     1200
tcaaatcatc atgccccta tgacctgggc tacacacgtg ctacaatgga tggtacaaag     1260
ggctgcaaga ccgcgaggtc aagccaatcc cataaaacca ttctcagttc ggattgtagg     1320
ctgcaactcg cctacatgaa gctggaatcg ctagtaatcg cggatcagca tgccgcggtg     1380
aatacgttcc cgggccttgt acacaccgcc cgtcacacca cgagagtttg taacacccga     1440
agtcggtggg gtaacctta tggagccagc cgcctaaggt gggacagatg attggggtga     1500
agtcgtaaca aggtagccgt atcggaaggt gcggctggat caccttccttt                1550

<210> SEQ ID NO 14
<211> LENGTH: 1505
<212> TYPE: DNA
<213> ORGANISM: Clostridium pasteurianum

<400> SEQUENCE: 14
aattgagagt ttgatcctgg ctcaggacga acgctggcgg cgtgcttaac acatgcaagt       60
cgagcgagaa accttcgggt ttctagcggc ggacgggtga gtaacacgtg gtaacctgc       120
ctcaaagagg ggaatagcct cccgaaaggg agattaatac cgcataatat tacagcttcg      180
catgaagcag taattaaagg agtaatccgc tttgagatgg acccgcggcg cattagctag      240
ttggagaggt aacggctcac caaggcgacg atgcgtagcc gacctgagag ggtgatcggc      300
cacattggaa ctgagacacg gtccagactc ctacgggagg cagcagtggg gaatattgca      360
caatgggcga aagcctgatg cagcaacgcc gcgtgagtga tgacggtctt cggattgtaa      420
agctctgtct tttgggacga taatgacggt accaaaggag gaagccacgg ctaactacgt      480
gccagcagcc gcggtaatac gtaggtggca agcgttgtcc ggatttactg ggcgtaaagg      540
atgtgtaggc ggatacttaa gtgagatgtg aaagccccgg gcttaacttg ggactgcat      600
ttcaaactgg gtgtctagag tgcaggagag gaaagcggaa ttcctagtgt agcggtgaaa      660
tgcgtagaga ttaggaagaa catcagtggc gaaggcggct ttctggactg taactgacgc      720
tgaggcatga aagcgtgggg agcaaacagg attagatacc ctggtagtcc acgccgtaaa      780
cgatgagtac taggtgtagg aggtatcgac tccttctgtg ccgcagtaaa cacaataagt      840
```

```
actccgcctg ggaagtacgg tcgcaagatt aaaactcaaa ggaattgacg ggggcccgca      900
caagcagcgg agcatgtggt ttaattcgaa gcaacgcgaa gaaccttacc tagacttgac      960
atctcctgaa tagcgtagag atacgtgaag cccttcgggg caggaagaca ggtggtgcat     1020
ggttgtcgtc agctcgtgtc gtgagatgtt gggttaagtc ccgcaacgag cgcaaccctt     1080
atcattagtt gctaccatta agttgagcac tctagtgaga ctgcccgggt taaccgggag     1140
gaaggcggga tgacgtcaa atcatcatgc cccttatgtc tagggctaca cacgtgctac     1200
aatggtgaga caacgagat gcaataccgc gaggtggagc caaacttgaa aactcatccc     1260
agttcggatt gtaggctgaa attcgcctac atgaagttgg agttgctagt aatcgcgaat     1320
cagaatgtcg cggtgaatac gttcccgggc cttgtacaca ccgcccgtca ccatgaga      1380 gctggtaaca cccgaagtcc gtgaggtaac ctttatggag ccagcggccg aaggtgggat     1440
tagtgattgg ggtgaagtcg taacaaggta gccgtaggag aacctgcggc tggatcacct     1500
cctttt                                                                 1505

<210> SEQ ID NO 15
<211> LENGTH: 1566
<212> TYPE: DNA
<213> ORGANISM: Virgibacillus halophilus

<400> SEQUENCE: 15
ttttggagag tttgatcttg gctcaggacg aacgctggcg gcgtgcctaa tacatgcaag       60
tcgagcgcgg gaagcaggat gatcctcatc tgaggtgatt cctgtggaac gagcggcgga      120
cgggtgagta acacgtgggc aacctgcctg taagatcggg ataactcgtg gaaacgcgag      180
ctaataccgg atgatacttt tcatcgcatg gtgagaagtt gaaagatggc tttaagctat      240
cacttacaga tgggcccgcg gcgcattagc tagttggtgg ggtaacggcc taccaaggca      300
acgatgcgta gccgacctga gagggtgatc ggccacactg ggactgagac acggcccaga      360
ctcctacggg aggcagcagt agggaatctt ccgcaatgga cgaaagtctg acggagcaac      420
gccgcgtgag tgatgaaggt tttcggatcg taaaactctg ttgtcaggga agaacaagtg      480
ccgtttgaat aaggcggcac cttgacggta cctgaccaga aagccccggc taactacgtg      540
ccagcagccg cggtaatacg taggggggcaa gcgttgtccg gaattattgg gcgtaaagcg      600
cgcgcaggcg gtcttttaag tctgatgtga agcccacgg cttaaccgtg gagggtcatt      660
ggaaactgga ggacttgagt gcagaagagg agagtggaat ccatgtgta gcggtgaaat      720 gcgtagagat atggaggaac accagtggcg aaggcgactc tctggtctgc aactgacgct      780
gaggcgcgaa agcgtgggta gcaacagga ttagataccc tggtagtcca cgccgtaaac      840
gatgagtgct agtgttagg gggtttccgc cccttagtgc tgaagttaac gcattaagca      900
ctccgcctgg ggagtacggc cgcaaggctg aaactcaaaa gaattgacgg gggcccgcac      960
aagcggtgga gcatgtggtt taattcgaag caacgcgaag aaccttacca ggtcttgaca     1020
tcctctgaca gccttagaga taaggtgttc ccttcgggga cagagtgaca ggtggtgcat     1080
ggttgtcgtc agctcgtgtc gtgagatgtt gggttaagtc ccgcaacgag cgcaaccctt     1140
gagattagtt gccagcatta agttgggcac tctaatctga ctgccggtga caaaccggag     1200
gaaggtgggg atgacgtcaa atcatcatgc cccttatgac ctgggctaca cacgtgctac     1260
aatggatggt acagagggaa gcgaagccgc gaggtgaagc aaatcccaca aaaccattct     1320
cagttcggat tgcaggctgc aactcgcctg catgaagccg gaatcgctag taatcgcgga     1380
```

| | |
|---|---|
| tcagcatgcc gcggtgaata cgttcccggg ccttgtacac accgcccgtc acaccacgag | 1440 |
| agttggtaac acccgaagtc ggtgaggtaa ccttttttgga gccagccgcc gaaggtggga | 1500 |
| cgaatgattg gggtgaagtc gtaacaaggt agccgtatcg gaaggtgcgg ctggatcacc | 1560 |
| tcctttt | 1566 |

<210> SEQ ID NO 16
<211> LENGTH: 1549
<212> TYPE: DNA
<213> ORGANISM: Bacillus licheniformis

<400> SEQUENCE: 16

| | |
|---|---|
| catggagagt ttgatcctgg ctcaggacga acgctggcgg cgtgcctaat acatgcaagt | 60 |
| cgagcggacc gacgggagct tgctccctta ggtcagcggc ggacgggtga gtaacacgtg | 120 |
| ggtaacctgc ctgtaagact gggataactc cgggaaaccg gggctaatac cggatgcttg | 180 |
| attgaaccgc atggttccaa tcataaaagg tggcttttag ctaccactta cagatggacc | 240 |
| cgcggcgcat tagctagttg gtgaggtaac ggctcaccaa ggcgacgatg cgtagccgac | 300 |
| ctgagagggt gatcggccac actgggactg agacacggcc cagactccta cgggaggcag | 360 |
| cagtagggaa tcttccgcaa tggacgaaag tctgacggag caacgccgcg tgagtgatga | 420 |
| aggttttcgg atcgtaaaac tctgttgtta gggaagaaca gtaccgttc gaatagggcg | 480 |
| gcaccttgac ggtacctaac cagaaagcca cggctaacta cgtgccagca gccgcggtaa | 540 |
| tacgtaggtg gcaagcgttg tccggaatta ttgggcgtaa agcgcgcgca ggcggttct | 600 |
| taagtctgat gtgaaagccc ccggctcaac cggggagggt cattggaaac tggggaactt | 660 |
| gagtgcagaa gaggagagtg gaattccacg tgtagcggtg aaatgcgtag agatgtggag | 720 |
| gaacaccagt ggcgaaggcg actctctggt ctgtaactga cgctgaggcg cgaaagcgtg | 780 |
| gggagcgaac aggattagat accctggtag tccacgccgt aaacgatgag tgctaagtgt | 840 |
| tagagggttt ccgcccttta gtgctgcagc aaacgcatta agcactccgc ctggggagta | 900 |
| cggtcgcaag actgaaactc aaaggaattg acggggcccc gcacaagcgg tggagcatgt | 960 |
| ggtttaattc gaagcaacgc gaagaacctt accaggtctt gacatcctct gacaaccta | 1020 |
| gagataggc ttccccttcg ggggcagagt gacaggtggt gcatggttgt cgtcagctcg | 1080 |
| tgtcgtgaga tgttgggtta agtcccgcaa cgagcgcaac ccttgatctt agttgccagc | 1140 |
| attcagttgg gcactctaag gtgactgccg gtgacaaacc ggaggaaggt ggggatgacg | 1200 |
| tcaaatcatc atgccccta tgacctggc tacacacgtg ctacaatggg cagaacaaag | 1260 |
| ggcagcgaag ccgcgaggct aagccaatcc cacaaatctg ttctcagttc ggatcgcagt | 1320 |
| ctgcaactcg actgcgtgaa gctggaatcg ctagtaatcg cggatcagca tgccgcggtg | 1380 |
| aatacgttcc cgggccttgt acaccgccc cgtcacacca cgagagtttg taacacccga | 1440 |
| agtcggtgag gtaacctttt ggagccagcc gccgaaggtg gacagatga ttggggtgaa | 1500 |
| gtcgtaacaa ggtagccgta tcggaaggtg cggctggatc acctcctttt | 1549 |

<210> SEQ ID NO 17
<211> LENGTH: 1523
<212> TYPE: DNA
<213> ORGANISM: Streptomyces griseus

<400> SEQUENCE: 17

| | |
|---|---|
| acggagagtt tgatcctggc tcaggacgaa cgctggcggc gtgcttaaca catgcaagtc | 60 |
| gaacgatgaa gcctttcggg gtggattagt ggcgaacggg tgagtaacac gtgggcaatc | 120 |

```
tgcccttcac tctgggacaa gccctggaaa cggggtctaa taccggataa cactctgtcc      180
cgcatgggac ggggttaaaa gctccggcgg tgaaggatga gcccgcggcc tatcagcttg      240
ttggtggggt aatggcctac caaggcgacg acgggtagcc ggcctgagag ggcgaccggc      300
cacactggga ctgagacacg gcccagactc ctacggagg cagcagtggg gaatattgca       360
caatgggcga aagcctgatg cagcgacgcc gcgtgaggga tgacggcctt cgggttgtaa      420
acctctttca gcagggaaga agcgagagtg acggtacctg cagaagaagc gccggctaac      480
tacgtgccag cagccgcggt aatacgtagg gcgcaagcgt tgtccggaat tattgggcgt      540
aaagagctcg taggcggctt gtcacgtcgg atgtgaaagc ccggggctta acccgggtc       600 tgcattcgat acgggctagc tagagtgtgg taggggagat cggaattcct ggtgtagcgg      660
tgaaatgcgc agatatcagg aggaacaccg gtggcgaagg cggatctctg ggccattact      720
gacgctgagg agcgaaagcg tggggagcga acaggattag ataccctggt agtccacgcc     780
gtaaacgttg ggaactaggt gttggcgaca ttccacgtcg tcggtgccgc agctaacgca     840
ttaagttccc cgcctgggga gtacggccgc aaggctaaaa ctcaaaggaa ttgacggggg      900
cccgcacaag cagcggagca tgtggcttaa ttcgacgcaa cgcgaagaac cttaccaagg     960
cttgacatat accggaaagc atcagagatg gtgccccct tgtggtcggt atacaggtgg     1020
tgcatggctg tcgtcagctc gtgtcgtgag atgttgggtt aagtcccgca acgagcgcaa    1080
cccttgttct gtgttgccag catgcccttc ggggtgatgg ggactcacag gagactgccg    1140
gggtcaactc ggaggaaggt ggggacgacg tcaagtcatc atgcccctta tgtcttgggc    1200
tgcacacgtg ctacaatggc cggtacaatg agctgcgatg ccgcgaggcg gagcgaatct    1260 caaaagccg gtctcagttc ggattgggt ctgcaactcg acccccatgaa gtcggagttg     1320 ctagtaatcg cagatcagca ttgctgcggt gaatacgttc ccgggccttg tacacaccgc    1380
ccgtcacgtc acgaaagtcg gtaacacccg aagccggtgg cccaacccct tgtgggaggg    1440
agctgtcgaa ggtgggactg gcgattggga cgaagtcgta acaaggtagc cgtaccggaa    1500
ggtgcggctg gatcacctcc ttt                                            1523
```